(12) United States Patent
Jiang et al.

(10) Patent No.: US 10,130,716 B2
(45) Date of Patent: *Nov. 20, 2018

(54) ZWITTERIONIC POLYMER BIOCONJUGATES AND RELATED METHODS

(71) Applicant: University of Washington through its Center for Commercialization, Seattle, WA (US)

(72) Inventors: Shaoyi Jiang, Redmond, WA (US); Andrew Keefe, Seattle, WA (US); Hong Xue, Pleasanton, CA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/526,846

(22) Filed: Oct. 29, 2014

(65) Prior Publication Data

US 2015/0157732 A1 Jun. 11, 2015

Related U.S. Application Data

(63) Continuation of application No. 13/463,677, filed on May 3, 2012, now Pat. No. 8,877,172, which is a continuation of application No. PCT/US2010/055886, filed on Nov. 8, 2010.

(60) Provisional application No. 61/259,088, filed on Nov. 6, 2009.

(51) Int. Cl.
*A61K 38/48* (2006.01)
*A61K 47/48* (2006.01)

(52) U.S. Cl.
CPC .... *A61K 47/48176* (2013.01); *A61K 38/4826* (2013.01); *C12Y 304/21001* (2013.01)

(58) Field of Classification Search
CPC .................. A61K 38/4826; A61K 47/48176
See application file for complete search history.

(56) References Cited

U.S. PATENT DOCUMENTS

| | | | |
|---|---|---|---|
| 2,777,872 A | 1/1957 | Shacklett | |
| 3,671,502 A | 6/1972 | Samour | |
| 4,075,183 A | 2/1978 | Kawakami | |
| 4,138,446 A | 2/1979 | Kawakami | |
| 4,415,388 A | 11/1983 | Korpman | |
| 4,493,926 A | 1/1985 | Williams, Jr. | |
| 4,569,798 A | 2/1986 | Nieh | |
| 4,985,023 A | 1/1991 | Blank | |
| 5,204,060 A | 4/1993 | Allenmark | |
| 5,695,552 A | 12/1997 | Taylor | |
| 5,714,360 A | 2/1998 | Swan | |
| 5,919,523 A | 7/1999 | Sundberg | |
| 5,986,042 A | 11/1999 | Irizato | |
| 6,361,768 B1 | 3/2002 | Galleguillos | |
| 6,486,333 B1 | 11/2002 | Murayama | |
| 6,864,314 B1 | 3/2005 | Yeung et al. | |
| 6,897,263 B2 | 5/2005 | Hell | |
| 6,924,338 B1 | 8/2005 | Davies et al. | |
| 7,056,532 B1 | 6/2006 | Kabanov | |
| 7,291,427 B2 | 11/2007 | Kawamura | |
| 7,306,625 B1 | 12/2007 | Stratford | |
| 7,335,248 B2 | 2/2008 | Abou-Nemeh | |
| 7,737,224 B2 | 6/2010 | Willis | |
| 8,617,592 B2* | 12/2013 | Jiang .................... | A61K 9/5153 424/450 |
| 8,877,172 B2* | 11/2014 | Jiang .................. | A61K 38/4826 424/78.18 |
| 9,535,062 B2* | 1/2017 | Jiang ................ | G01N 33/54353 |
| 2003/0195133 A1 | 10/2003 | Shefer et al. | |
| 2004/0063587 A1 | 4/2004 | Horton | |
| 2004/0063881 A1 | 4/2004 | Lewis | |
| 2004/0067503 A1 | 4/2004 | Tan et al. | |
| 2005/0004661 A1 | 1/2005 | Lewis et al. | |
| 2005/0058689 A1 | 3/2005 | McDaniel | |
| 2006/0183863 A1 | 8/2006 | Huang | |
| 2006/0217285 A1 | 9/2006 | Destarac | |
| 2006/0240072 A1 | 10/2006 | Chudzik | |
| 2007/0021569 A1 | 1/2007 | Willis et al. | |
| 2007/0042198 A1 | 2/2007 | Schonemyr | |
| 2007/0104654 A1 | 5/2007 | Hsieh | |
| 2008/0130393 A1 | 6/2008 | Kanasugi | |
| 2008/0131393 A1 | 6/2008 | Yeung et al. | |
| 2008/0181861 A1 | 7/2008 | Jiang | |
| 2008/0299177 A1 | 12/2008 | Hardy | |
| 2009/0156460 A1* | 6/2009 | Jiang et al. ........................ | 514/2 |
| 2009/0197791 A1 | 8/2009 | Balastre | |

FOREIGN PATENT DOCUMENTS

| DE | 10 2006 004 111 A1 | 8/2007 |
|---|---|---|
| EP | 0 354 984 A2 | 2/1990 |
| EP | 0 419 654 A1 | 4/1991 |
| EP | 0 479 245 A2 | 4/1992 |

(Continued)

OTHER PUBLICATIONS

Jiang et al. (Analytical Chemistry, vol. 80, No. 20, published Oct. 15, 2008, pp. 7894-7901 and Supplemental Information).*
Becker, M.L., et al., "Peptide-Polymer Bioconjugates: Hybrid Block Copolymers Generated via Living Radical Polymerizations From Resin-Supported Peptides," Chemical Communications 2:180-181, Jan. 2003.
Berge, S.M., et al., "Pharmaceutical Salts," Journal of Pharmaceutical Sciences 66(1):1-19, Jan. 1977.
"Betaine," Wikipedia, The Free Encyclopedia, <http://en.wikipedia.org/wiki/Betaine> [retrieved Jul. 31, 2011], 1 page.
"Bromide," Wikipedia, The Free Encyclopedia, <http://en.wikipedia.org/wiki/Bromide> [retrieved Jul. 27, 2011], 3 pages.
Chang, Y., et al., "Highly Protein-Resistant Coatings From Well-Defined Diblock Copolymers Containing Sulfobetaines," Langmuir 22(5):2222-2226, Feb. 2006.
Chen, S., et al., "Controlling Antibody Orientation on Charged Self-Assembled Monolayers," Langmuir 19(7):2859-2864, Apr. 2003.

(Continued)

*Primary Examiner* — Alma Pipic
(74) *Attorney, Agent, or Firm* — Christensen O'Connor Johnson Kindness PLLC

(57) ABSTRACT

Zwitterionic polymer and mixed charge copolymer bioconjugates, methods for making and using the bioconjugates.

7 Claims, 8 Drawing Sheets

Specification includes a Sequence Listing.

(56) References Cited

FOREIGN PATENT DOCUMENTS

| | | |
|---|---|---|
| FR | 2894585 A1 | 6/2007 |
| FR | 2898067 A1 | 9/2007 |
| JP | 51-147581 A | 12/1976 |
| JP | 53-124538 | 10/1978 |
| JP | 59-199696 A | 11/1984 |
| JP | 63-234007 A | 9/1988 |
| JP | 03-166272 A | 7/1991 |
| JP | 06-118399 A | 4/1994 |
| JP | 10-330687 A | 12/1998 |
| JP | 2000-265110 A | 9/2000 |
| JP | 2001-294810 A | 10/2001 |
| JP | 2003-504476 A | 6/2002 |
| JP | 2007-130194 A | 5/2007 |
| JP | 2009-528440 A | 9/2007 |
| JP | 2009-102314 A | 5/2009 |
| SU | 178063 A1 | 12/1992 |
| SU | 1780673 A1 | 12/1992 |
| WO | 00/39176 A1 | 7/2000 |
| WO | 2004/058837 A2 | 7/2004 |
| WO | 2004/100666 A1 | 11/2004 |
| WO | 2007/024393 A2 | 3/2007 |
| WO | 2007/068744 A1 | 6/2007 |
| WO | 2007/099239 A2 | 9/2007 |
| WO | 2008/019381 A1 | 2/2008 |
| WO | 2008/083390 A2 | 7/2008 |
| WO | 2008/130296 A1 * | 10/2008 |
| WO | 2009/062947 A1 * | 5/2009 |
| WO | 2009/067562 A1 | 5/2009 |
| WO | 2010/096422 A1 | 8/2010 |

OTHER PUBLICATIONS

Chen, S., et al., "Strong Resistance of Oligo(phosphorylcholine) Self-Assembled Monolayers to Protein Adsorption," Langmuir 22(6):2418-2421, Mar. 2006.

Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.

Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.

Feng, W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12):2931-2942, Jun. 2004.

International Preliminary Report on Patentability and Written Opinion dated Jul. 14, 2011, issued in corresponding International Application No. PCT/US2010/055886, filed Nov. 8, 2010, 5 pages.

International Search Report and Written Opinion dated Jul. 14, 2011, issued in corresponding International Application No. PCT/US2010/055886, filed Nov. 8, 2010, 7 pages.

International Preliminary Report on Patentability dated May 8, 2012, issued in International Application No. PCT/US2010/055887, filed Nov. 8, 2010, 8 pages.

International Search Report and Written Opinion dated Jul. 28, 2011, issued in International Application No. PCT/US2010/055887, filed Nov. 8, 2010, 12 pages.

Jiang, Y., et al., "Blood Compatibility of Polyurethane Surface Grafted Copolymerization With Sulfobetaine Monomer," Colloids and Surfaces B: Biointerfaces 36(1):27-33, Jul. 2004.

Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.

Juo, P.-S., "Concise Dictionary of Biomedicine and Molecular Biology," 2d ed., CRC Press, Boca Raton, Fla., 2002, "Biomolecule," p. 73.

Lewis, A., et al., "Poly(2-methacryloyloxyethyl phosphorylcholine) for Protein Conjugation," Bioconjugate Chemistry 19(11):2144-2155, Nov. 2008.

Li, L., et al., "Protein Adsorption on Alkanethiolate Self-Assembled Monolayers: Nanoscale Surface Structural and Chemical Effects," Langmuir 19(7):2974-2982, Apr. 2003.

Li, L., et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.

Lowe, A.B., et al., "Well-Defined Sulfobetaine-Based Statistical Copolymers as Potential Antibioadherent Coatings," Journal of Biomedical Materials Research 52(1):88-94, Jul. 2000.

"Nail Infections," Health911, <http://www.health911.com/nail-infections> [retrieved Aug. 29, 2011], 3 pages.

Notification of the First Office Action dated Aug. 21, 2013, issued in corresponding Chinese Application No. 201080055964.6, filed Nov. 8, 2010, 8 pages.

Ramanathan, S., et al., "Targeted PEG-Based Bioconjugates Enhance the Cellular Uptake and Transport of a HIV-1 TAT Nonapeptide," Journal of Controlled Release 77(3):199-212, Dec. 2001.

West, S.L., et al., "The Biocompatibility of Crosslinkable Copolymer Coatings Containing Sulfobetaines and Phosphobetaines," Biomaterials 25:1195-1204, Apr. 2004.

Yuan, J., et al., "Platelet Adhesion Onto Segmented Polyurethane Surfaces Modified by Carboxybetaine," Journal of Biomaterial Science, Polymer Edition 14(12):1339-1349, Dec. 2003.

Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.

Yuan, J., et al., "Improvement of Blood Compatibility on Cellulose Membrane Surface by Grafting Betaines," Colloids and Surfaces B: Biointerfaces 30(1-2):147-155, Jul. 2003.

Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.

Yuan, Y., et al., "Grafting Sulfobetaine Monomer Onto Silicone Surface to Improve Haemocompatability," Polymer International 53(1):121-126, Jan. 2004.

Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.

Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.

Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.

Zhang, L.-M., et al., "New Water-Soluble Ampholytic Polysaccharides for Oilfield Drilling Treatment: A Preliminary Study," Carbohydrate Polymers 44(3):255-260, Mar. 2001.

Zhang, Z., et al., "Surface Grafted Sulfobetaine Polymers via Atom Transfer Radical Polymerization as Superlow Fouling Coatings," Journal of Physical Chemistry B 110(22):10799-10804, Jun. 2006.

Zhang, Z., et al., "Superlow Fouling Sulfobetaine and Carboxybetaine Polymers on Glass Slides," Langmuir 22(24):10072-10077, Nov. 2006.

Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.

Zheng, J., et al., "Molecular Simulation Study of Water Interactions With Oligo (Ethylene Glycol)-Terminated Alkanethiol Self-Assembled Monolayers," Langmuir 20(20):8931-8938, Sep. 2004.

Zheng, J., et al., "Strong Repulsive Forces Between Protein and Oligo (Ethylene Glycol) Self-Assembled Monolayers: A Molecular Simulation Study," Biophysical Journal 89(1):158-166, Jul. 2005.

Zhou, J., et al., "Platelet Adhesion and Protein Adsorption on Silicone Rubber Surface by Ozone-Induced Grafted Polymerization With Carboxybetaine Monomer," Colloids and Surfaces B: Biointerfaces 41(1):55-62, Mar. 2005.

Office Action dated Oct. 28, 2014, issued in corresponding Application No. JP2012-538070, filed Nov. 8, 2010, 3 pages.

(56) References Cited

OTHER PUBLICATIONS

Partial Supplementary European Search Report dated Sep. 17, 2015, issued in corresponding European Patent Application No. 10829255. 8, filed Nov. 8, 2010, 4 pages.
Zhang, Z., et al., "Dual-Functional Biomimetic Materials: Nonfouling Poly(carboxybetaine) With Active Functional Groups for Protein Immobilization," Biomacromolecules 7(12):3311-3315, 2006.
Jiang, S., and Z. Cao, "Ultralow-Fouling, Functionalizable, and Hydrolyzable Zwitterionic Materials and Their Derivatives for Biological Applications," Advanced Materials 22(9):920-932, Mar. 2010.
Johnston, E.E., et al., "Interactions Between Pseudomonas aeruginosa and Plasma-Deposited PEO-Like Thin Films During Initial Attachment and Growth," American Chemical Society Polymer Preprints, 38(1):1016-1017, Apr. 1997.
Kawabata, N., et al., "Removal of Micro-Organisms by Filtration Through Unwoven Cloth Coated With a Pyridinium-Type Polymer," Epidemiology and Infection 108(1):123-134, Feb. 1992.
Kenawy, E.-R., et al., "The Chemistry and Applications of Antimicrobial Polymers: A State-of-the-Art Review," Biomacromolecules 8(5):1359-1384, May 2007.
Kingshott, P., et al., "Covalent Attachment of Poly(ethylene glycol) to Surfaces, Critical for Reducing Bacterial Adhesion," Langmuir 19(17):6912-6921, Jul. 2003.
Klibanov, A.M., "Permanently Microbicidal Materials Coatings," Journal of Materials Chemistry 17(24):2479-2482, May 2007.
Kuroda, K., and W.F. DeGrado, "Amphiphilic Polymethacrylate Derivatives as Antimicrobial Agents," Journal of the American Chemical Society 127(12):4128-4129, Mar. 2005.
Ladd, J., et al., "Zwitterionic Polymers Exhibiting High Resistance to Nonspecific Protein Adsorption From Human Serum and Plasma," Biomacromolecules 9(5):1357-1361, May 2008.
Ledley, F.D., "Nonviral Gene Therapy: The Promise of Genes as Pharmaceutical Products," Human Gene Therapy 6(9):1129-1144, Sep. 1995.
Lee, J.H., et al., "Polyplexes Assembled With Internally Quaternized PAMAM-OH Dendrimer and Plasmid DNA Have a Neutral Surface and Gene Delivery Potency," Bioconjugate Chemistry 14(6):1214-1221, Nov.-Dec. 2003.
Lee, S.B., et al., "Permanent, Nonleaching Antibacterial Surfaces. 1. Synthesis by Atom Transfer Radical Polymerization," Biomacromolecules 5(3):877-882, Feb. 2004.
Lewis, A.L. "Phosphorylcholine-Based Polymers and Their Use in the Prevention of Biofouling," Colloids and Surfaces B: Biointerfaces 18(3-4):261-275, Oct. 2000.
Li, G., et al., "Ultra Low Fouling Zwitterionic Polymers With a Biomimetic Adhesive Group," Biomaterials 29(35):4592-4597, Dec. 2008.
Li, G., et al., "Ultralow Fouling Zwitterionic Polymers Grafted From Surfaces Covered With an Initiator Via an Adhesive Mussel Mimetic Linkage," Journal of Physical Chemistry B 112(48):15269-15274, Nov. 2008.
Li, L., et al., "Protein Interactions With Oligo(ethylene glycol) (OEG) Self-Assembled Monolayers: OEG Stability, Surface Packing Density and Protein Adsorption," Journal of Biomaterials Science, Polymer Edition 18(11):1415-1427, 2007.
Lindstedt, M., et al., "Antimicrobial Activity of Betaine Esters, Quaternary Ammonium Amphiphiles Which Spontaneously Hydrolyze Into Nontoxic Components," Antimicrobial Agents and Chemotherapy 34(10):1949-1954, Oct. 1990.
Loose, C., et al., "A Linguistic Model for the Rational Design of Antimicrobial Peptides," Nature 443(7113):867-869, Oct. 2006.
Lowe, A.B.., and C.L. McCormick, "Synthesis and Solution Properties of Zwitterionic Polymers," Chemical Reviews 102(11):4177-4189, Nov. 2002.
Luo, D., and W.M. Saltzman, "Synthetic DNA Delivery Systems," Nature Biotechnology 18(1):33-37, Jan. 2000.
Lynn, D.M., and R. Langer, "Degradable Poly(β-amino esters): Synthesis, Characterization, and Self-Assembly With Plasmid DNA," Journal of the American Chemical Society 122(44):10761-10768, Oct. 2000.
Ma, H., et al., "'Non-Fouling' Oligo(ethylene glycol)-Functionalized Polymer Brushes Synthesized by Surface-Initiated Atom Transfer Radical Polymerization," Advanced Materials 16(4):338-341, Feb. 2004.
Notice of Reasons for Rejection dated Jul. 25, 2013, issued in corresponding Japanese Application No. 2010-534290, filed Nov. 19, 2008, 7 pages.
Nyyssölä, A., "Pathways of Glycine Betaine Synthesis in Two Extremely Halophilic Bacteria, Actinopolyspora halophila and Ectothiorhodospira halochloris," doctoral dissertation, Department of Chemical Technology, Helsinki University of Technology, Espoo, Finland, Oct. 2001, 68 pages.
Ostuni, E., et al., "Self-Assembled Monolayers That Resist the Adsorption of Proteins and the Adhesion of Bacterial and Mammalian Cells," Langmuir 17(20):6336-6343, Aug. 2001.
Ostuni, E., et al., "A Survey of Structure-Property Relationships of Surfaces That Resist the Adsorption of Protein," Langmuir 17(18):5605-5620, Jul. 2001.
Overney, R.M., et al., "Compliance Measurements of Confined Polystyrene Solutions by Atomic Force Microscopy," Physical Review Letters 76(8):1272-1275, Feb. 1996.
Pasquier, N., et al., "From Multifunctionalized Poly(ethylene imine)s Toward Antimicrobial Coatings," Biomacromolecules 8(9):2874-2882, Sep. 2007.
Patel, J.D., et al., "Phospholipid Polymer Surfaces Reduce Bacteria and Leukocyte Adhesion Under Dynamic Flow Conditions," Journal of Biomedical Materials Research, Part A 73A(3):359-366, Jun. 2005.
Patent Examination Report No. 1 dated May 28, 2013, issued in corresponding Australian Application No. 2008326438, filed Nov. 19, 2008, 3 pages.
Prata, C.A.H., et al., "Charge-Reversal Amphiphiles for Gene Delivery," Journal of the American Chemical Society 126(39):12196-12197, Oct. 2004.
Roland, C.M., and R. Casalini, "Temperature Dependence of Local Segmental Motion in Polystyrene and Its Variation With Molecular Weight," Journal of Chemical Physics 119(3):1838-1842, Jul. 2003.
Roosjen, A., et al., "Microbial Adhesion to Poly(ethylene oxide) Brushes: Influence of Polymer Chain Length and Temperature," Langmuir 20(25):10949-10955, Nov. 2004.
Russell, T.P., "Surface-Responsive Materials," Science 297(5583):964-967, Aug. 2002.
Schumacher, J.F., et al., "Engineered Antifouling Microtopographies—Effect of Feature Size, Geometry, and Roughness on Settlement of Zoospores of the Green Alga Ulva," Biofouling 23(1):55-62, 2007.
Shen, M., et al., "PEO-Like Plasma Polymerized Tetraglyme Surface Interactions With Leukocytes and Proteins: In Vitro and In Vivo Studies," Journal of Biomaterials Science, Polymer Edition 13(4):367-390, 2002.
Shikuma, N.J., and M.G. Hadfield, "Temporal Variation of an Initial Marine Biofilm Community and Its Effects on Laval Settlement and Metamorphosis of the Tubeworm Hydroides elegans," Biofilms 2(4):231-238, Oct. 2005.
Sills, S., et al., "Molecular Dissipation Phenomena of Nanoscopic Friction in the Heterogeneous Relaxation Regime of a Glass Former," Journal of Chemical Physics 123:134902, Oct. 2005, 7 pages.
Tegoulia, V.A., and S.L. Cooper, "*Staphylococcus aureus* Adhesion to Self-Assembled Monolayers: Effect of Surface Chemistry and Fibrinogen Presence," Colloids and Surfaces B: Biointerfaces 24(3-4):217-228, Apr. 2002.
Tiller, J.C., et al., "Designing Surfaces That Kill Bacteria on Contact," Proceedings of the National Academy of Sciences USA (PNAS) 98(11):5981-5985, May 2001.
Tsai, W.-B., et al., "Human Plasma Fibrinogen Adsorption and Platelet Adhesion to Polystyrene," Journal of Biomedical Materials Research 44(2):130-139, Feb. 1999.

(56) References Cited

OTHER PUBLICATIONS

Ueda, T., et al., "Preparation of 2-Methacryloyloxyethyl Phosphorylcholine Copolymers With Alkyl Methacrylates and Their Blood Compatibility," Polymer Journal 24(11):1259-1269, Nov. 1992.
Ueland, P.M., et al., "Betaine: A Key Modulator of One-Carbon Metabolism and Homocysteine Status," Clinical Chemistry and Laboratory Medicine 43(10):1069-1075, Oct. 2005.
Vaisocherová, H., et al., "Ultralow Fouling and Functionalizable Surface Chemistry Based on a Zwitterionic Polymer Enabling Sensitive and Specific Protein Detection in Undiluted Blood Plasma," Analytical Chemistry 80(20):7894-7901, Oct. 2008.
Vallee-Rehel, K., et al., "A New Approach in the Development and Testing of Antifouling Paints Without Organotin Derivatives," Journal of Coatings Technology 70(880):55-63, May 1998.
Wei, J.H., et al., "Direct Measurement of Nanofluxes and Structural Relaxations of Perfluorinated Ionomer Membranes by Scanning Probe Microscopy," Journal of Membrane Science 279(1-2):608-614, Aug. 2006.
Wolfert, M.A., et al., "Polyelectrolyte Vectors for Gene Delivery: Influence of Cationic Polymer on Biophysical Properties of Complexes Formed With DNA," Bioconjugate Chemistry 10(6):993-1004, Nov.-Dec. 1999.
Wright, M.R., "Arrhenius Parameters for the Alkaline Hydrolysis of Esters in Aqueous Solution. Part III. Methyl Betaine Methyl Ester," Journal of the Chemical Society B: Physical Organic, 1968, pp. 548-550.
Yang, W., et al., "Film Thickness Dependence of Protein Adsorption From Blood Serum and Plasma Onto Poly(sulfobetaine)-Grafted Surfaces," Langmuir 24(17):9211-9214, Aug. 2008.
Yang, W., et al., "Functionalizable and Ultra Stable Nanoparticles Coated With Zwitterionic Poly(carboxybetaine) in Undiluted Blood Serum," Biomaterials 30(29):5617-5621, Oct. 2009.
Yang, W., et al., "Pursuing 'Zero' Protein Adsorption of Poly(carboxybetaine) From Undiluted Blood Serum and Plasma," Langmuir 25(19):11911-11916, Jul. 2009.
Yebra, D.M., et al., "Antifouling Technology—Past, Present and Future Steps Towards Efficient and Environmentally Friendly Antifouling Coatings," Progress in Organic Coatings 50(2):75-104, Jul. 2004.
Zauner, W., et al., "Polylysine-Based Transfection Systems Utilizing Receptor-Mediated Delivery," Advanced Drug Delivery Reviews 30(1-3):97-113, Mar. 1998.
Zhang, L., et al., "Imaging and Cell Targeting Characteristics of Magnetic Nanoparticles Modified by a Functionalizable Zwitterionic Polymer With Adhesive 3,4-Dihydroxyphenyl-L-alanine Linkages," Biomaterials 31(25):6582-6588, Sep. 2010.
Zhang, Z., et al., "Biocompatible, Functionalizable, and Nonfouling Surfaces and Materials for Biomedical and Engineering Applications," doctoral dissertation, University of Washington, Seattle, 2008, 214 pages.
Zhang, Z., et al., "Nonfouling Behavior of Polycarboxybetaine-Grafted Surfaces: Structural and Environmental Effects," Biomacromolecules 9(10):2686-2692, Sep. 2008.
Zhang, Z., et al., "Polysulfobetaine-Grafted Surfaces as Environmentally Benign Ultralow Fouling Marine Coatings," Langmuir 25(23):13516-13521, Aug. 2009.
Zuidam, N.J., et al., "Effects of Physicochemical Characteristics of Poly(2-(dimethylamino)ethyl methacrylate)-Based Polyplexes on Cellular Association and Internalization," Journal of Drug Targeting 8(1):51-66, Jan. 2000.
Abel, T., et al., "Preparation and Investigation of Antibacterial Carbohydrate-Based Surfaces," Carbohydrate Research 337(24)1495-2499, Nov. 2002.
Ahlström, B., and L. Edebo, "Hydrolysis of the Soft Amphiphilic Antimicrobial Agent Tetradecyl Betainate Is Retarded After Binding to and Killing *Salmonella typhimurium*," Microbiology 144(9):2497-2504, Sep. 1998.
Ahlström, B., et al., "The Effect of Hydrocarbon Chain Length, pH, and Temperature on the Binding and Bactericidal Effect of Amphi-philic Betaine Esters on *Salmonella typhimurium*," Acta Pathologica Microbiologica et Immunologica Scandinavica 107(3):318-324, Mar. 1999.
Akesso, L., et al., "Deposition Parameters to Improve the Fouling-Release Properties of Thin Siloxane Coatings Prepared by PACVD," Applied Surface Science 255(13-14):6508-6514, Apr. 2009.
Al-Lohedan, H.A., "Reactions of Betaine Esters With Hydroxide Ion in Surfactant With Reactive and Unreactive Counterions," Tetrahedron 43(2):345-350, 1987.
Brault, N.D., et al., "Ultra-Low Fouling and Functionalizable Zwitterionic Coatings Grafted Onto $SiO_2$ Via a Biomimetic Adhesive Group for Sensing and Detection in Complex Media," Biosensors & Bioelectronics 25(10):2276-2282, Jun. 2010.
Breiting, V., et al., "A Study on Patients Treated With Polyacrylamide Hydrogel Injection for Facial Corrections," Aesthetic Plastic Surgery 28(1):45-53, Jan. 2004.
Bronich, T.K., et al., "Recognition of DNA Topology in Reactions Between Plasmid DNA and Cationic Copolymers," Journal of the American Chemical Society 122(35):8339-8343, Sep. 2000.
Cao, L., et al., "Glow Discharge Plasma Treatment of Polyethylene Tubing With Tetraglyme Results in Ultralow Fibrinogen Adsorption and Greatly Reduced Platelet Adhesion," Journal of Biomedical Materials Research Part A 79A(4):788-803, Dec. 2006.
Chang, Y., et al., "Development of Biocompatible Interpenetrating Polymer Networks Containing a Sulfobetaine-Based Polymer and a Segmented Polyurethane for Protein Resistance," Biomacromolecules 8(1):122-127,2007.
Chang, Y., et al., "A Systematic SPR Study of Human Plasma Protein Adsorption Behavior on the Controlled Surface Packing of Self-Assembled Poly(ethylene oxide) Triblock Copolymer Surfaces," Journal of Biomedical Materials Research Part A 93A(1):400-408, Apr. 2010.
Chen, G.H. and A.S. Hoffman, "Graft-Copolymers That Exhibit Temperature-Induced Phase-Transitions Over a Wide-Range of pH," Nature 373(6509):49-52, Jan. 1995.
Cheng, G., et al., "Inhibition of Bacterial Adhesion and Biofilm Formation on Zwitterionic Surfaces," Biomatenals 28(29):4192-4199, Oct. 2007.
Cheng, G., et al., "A Switchable Biocompatible Polymer Surface With Self-Sterilizing and Non-Fouling Capabilities," Angewandte Chemie International Edition 47(46):8831-8834, 2008.
Cheng G. et al., "Zwitterionic Carboxybetaine Polymer Surfaces and Their Resistance to Long-Term Biofilm Formation," Biomaterials 30(28):5234-5240, Oct. 2009.
Cheng, J., et al., "Formulation of Functionalized PLGA-PEG Nanoparticles for In Vivo Targeted Drug Delivery," Biomaterials 28(5):869-876, Feb. 2007.
Chung, K.K., et al., "Impact of Engineered Surface Microtopography on Biofilm Formation of *Staphylococcus aureus*," Biointerphases 2(2):89-94, Jun. 2007.
Cogan, N.G., "Two-Fluid Model of Biofilm Disinfection," Bulletin of Mathematical Biology 70(3):800-819, Apr. 2008.
Communication from Mexican Associate dated Jan. 17, 2014, that a second Office Action was issued by the Mexican Institute of Industrial Property in related Mexican Application No. MX/a/2010/005295, filed Nov. 19, 2008, 5 pages.
Communication Pursuant to Article 94(3) EPC, dated Oct. 19, 2010, issued in corresponding European Application No. 08851463.3, filed Nov. 19, 2008, 4 pages.
Database WPI, Week 199351 Thomson Scientific, London, AN 1993-412215 and SU 1780673 A1 (Centr Asia Sericulture Res Inst), Dec. 15, 1992.
Eberl, H.J., and R. Sudarsan, "Exposure of Biofilms to Slow Flow Fields: The Convective Contribution to Growth and Disinfection," Journal of Theoretical Biology 253(4):788-807, Aug. 2008.
Edebo, L., et al., "Betaine Esters: Quaternary Ammonium Compounds With Time-Limited Activity," Proceedings of the Industrial Applications of Surfactants III, Royal Society of Chemistry, University of Salford, U.K., Sep. 16-18, 1991, Special Publication No. 107, 1992, pp. 184-207.
Extended European Search Report dated Nov. 2, 2010, issued in European Application No. EP 08851866.7, filed Nov. 19, 2008, 4 pages.

(56) References Cited

OTHER PUBLICATIONS

First Examination Report dated Sep. 22, 2015, issued in corresponding Indian Application No. 2206/KOLNP/2010, filed Jun. 17, 2010, 2 pages.
Gaberc-Porekar, V., et al., "Obstacles and Pitfalls in the PEGylation of Therapeutic Proteins," Current Opinion in Drug Discovery & Development 11(2):242-250, Mar. 2008.
Gao, C.L., et al. "Functionalizable and Ultra-Low Fouling Zwitterionic Surfaces Via Adhesive Mussel Mimetic Linkages," Biomaterials 31(7):1486-1492, Mar. 2010.
Gottenbos, B., et al., "In Vitro and in Vivo Antimicrobial Activity of Covalently Coupled Quaternary Ammonium Silane Coatings on Silicone Rubber," Biomaterials 23(6):1417-1423, Mar. 2002.
Gray, T., et al., "Molecular Mobility and Transitions in Complex Organic Systems Studied by Shear Force Microscopy," Nanotechnology 18(4):044009, Jan. 2007, 9 pages.
Green, R.J., et al., "Adsorption of PEO-PPO-PEO Triblock Copolymers at the Solid/Liquid Interface: A Surface Plasmon Resonance Study," Langmuir 13(24):6510-6515, Nov. 1997.
Haldar, J., et al., "Polymeric Coatings That Inactivate Both Influenza Virus and Pathogenic Bacteria," Proceedings of be National Academy of Sciences USA (PNAS) 103(47):17667-17671, Nov. 2006.
Harder, P., et al., "Molecular Conformation in Oligo(ethylene glycol)-Terminated Self-Assembled Monolayers on Gold and Silver Surfaces Determines Their Ability to Resist Protein Adsorption," Journal of Physical Chemistry B 102(2):426-436, Jan. 1998.
He, M., et al., "Effect of Interfacial Liquid Structuring on the Coherence Length in Nanolubrication," Physical Review Letters 88(15):154302, Apr. 2002, 4 pages.
He, Y., et al., "Molecular Simulation Studies of Protein Interactions With Zwitterionic Phosphorylcholine Self- Assembled Monolayers in the Presence of Water," Langmuir 24(18):10358-10364, Aug. 2008.
He, Y., et al., "Origin of Repulsive Force and Structure/Dynamics of Interfacial Water in OEG-Protein Interactions: A Molecular Simulation Study," Physical Chemistry Chemical Physics 10(36):5539-5544, Aug. 2008.
Herold, D.A., et al., "Oxidation of Polyethylene Glycols by Alcohol Dehydrogenase," Biochemical Pharmacology 38(1):73-76, Jan. 1989.
Hirota, K., et al., "Coating of a Surface With 2-Methacryloyloxyethyl Phosphorylcholine (MPC) Co-Polymer Significantly Reduces Retention of Human Pathogenic Microorganisms," FEMS Microbiology Letters 248(1):37-45, Jul. 2005.
Holmberg, K., et al., "Effects on Protein Adsorption, Bacterial Adhesion and Contact Angle of Grafting PEG Chains to Polystyrene," Journal of Adhesion Science and Technology 7(6):503-517, Jun. 1993.
Holmlin, R.E., et al., "Zwitterionic SAMs That Resist Nonspecific Adsorption of Protein From Aqueous Buffer," Langmuir 17(9):2841-2850, Apr. 2001.
Horbett, T.A., "Principles Underlying the Role of Adsorbed Plasma Proteins in Blood Interactions With Foreign Materials," Cardiovascular Pathology 2(Suppl. 3):137S-148S, Jul.-Sep. 1993.
Horbett, T.A., et al., "The Role of Adsorbed Proteins in Animal Cell Adhesion," Colloids and Surfaces B: Biointerfaces 2(1-3):225-240, Mar. 1994.
Huang, S., and M.G. Hadfield, "Composition and Density of Bacterial Biofilms Determine Larval Settlement of the Polychaete Hydroides elegans," Marine Ecology Progress Series 260:161-172, Sep. 2003.
Hutter, J.L., and J. Bechhoefer, et al., "Measurement and Manipulation of van der Walls Forces in Atomic-Force Microscopy," Journal of Vacuum Science & Technology B 12(3):2251-2253, May-Jun. 1994.
Huxtable, R.J., "Physiological Actions of Taurine," Physiological Reviews 72(1):101-163, Jan. 1992.
Ilker, M.F., et al., "Tuning the Hemolytic and Antibacterial Activities of Amphiphilic Polynorbornene Derivatives," Journal of the American Chemical Society 126(48):15870-15875, Dec. 2004.
International Preliminary Report on Patentability dated Jun. 3, 2010, issued in corresponding International Application No. PCT/US2008/084098, filed Nov. 19, 2008, 8 pages.
International Search Report and Written Opinion dated Jul. 7, 2009, issued in corresponding International Application No. PCT/US2008/084098, filed Nov. 19, 2008, 10 pages.
International Search Report and Written Opinion dated Jan. 29, 2009, issued in International Application No. PCT/US2008/084095, filed Nov. 19, 2008, 12 pages.
Ishihara, K., et al., "Inhibition of Fibroblast Cell Adhesion on Substrate by Coating With 2-Methacryloyloxyethyl Phosphorylcholine Polymers," Journal of Biomaterials Science, Polymer Edition 10(10):1047-1061, 1999.
Japanese Office Action dated Apr. 24, 2013, issued in Japanese Application No. 2010-534289, filed Nov. 19, 2008, 12 pages.

* cited by examiner

SEQUENCE LISTING

<160> NUMBER OF SEQ ID NOS: 1

<210> SEQ ID NO 1
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein the X at position 1 is N-Succinyl
<220> FEATURE:
<221> NAME/KEY: MISC_FEATURE
<222> LOCATION: (6)..(6)
<223> OTHER INFORMATION: Wherein the X at position 6 is p-nitroanilide

<400> SEQUENCE: 1

Xaa Ala Ala Pro Phe Xaa
1               5

ZWITTERIONIC POLYMER BIOCONJUGATES AND RELATED METHODS

CROSS-REFERENCE TO RELATED APPLICATION

This application is a continuation of U.S. application Ser. No. 13/463,677, filed May 3, 2012, which is a continuation of International Application No. PCT/US2010/055886, filed Nov. 8, 2010, which claims the benefit of U.S. Provisional Application No. 61/259,088, filed Nov. 6, 2009, all of which are expressly incorporated herein by reference in their entirety.

STATEMENT OF GOVERNMENT LICENSE RIGHTS

This invention was made with Government support under Contract No. N000140910137 awarded by the Office of Naval Research and Contract No. DMR-0705907 awarded by the National Science Foundation. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 52879_Sequence_Final_2014-10-03.txt. The text file is 1 KB; was created on Oct. 3, 2014; and is being submitted via EFS-Web with the filing of the specification.

BACKGROUND OF THE INVENTION

Protein and peptide therapeutic agents comprise an increasing share of the pharmaceutical market with biological drugs making up about $4.5 billion in U.S. sales in 2008. Among these biological drugs are monoclonal antibodies, hormones, and therapeutic enzymes.

Despite the growth of the biopharmaceutical market, implementation of therapeutic proteins remains a challenging task. The inherent physical and chemical instability of proteins can lead to conformational changes, degradation, aggregation, precipitation, and adsorption onto surfaces, each of which can diminish the protein's activity or render it completely inactive.

Once administered, therapeutic proteins are susceptible to short half lives, proteolysis, opsonization, and can cause immunogenic responses, each resulting in undesirable pharmacokinetics. A variety of technologies have been developed to improve these shortfalls. Included among these technologies are amino acid manipulation, genetic fusion of immunoglobulin domains or serum proteins, and conjugation with natural and synthetic polymers.

One successful implementation is the covalent conjugation of the therapeutic protein with polyethylene glycol (PEG), a non-toxic, non-immunogenetic polymer. The process of conjugation of PEG to the therapeutic protein is commonly referred to as PEGylation. PEGylation is known to change the physical and chemical properties of the biomolecule, including conformation, electrostatic binding, and hydrophobicity, and can result in improved pharmacokinetic properties for the drug. Advantages of PEGylation include improvements in drug solubility and diminution of immunogenicity, increased drug stability and circulatory life once administered, and reductions in proteolysis and renal excretion, which allows for reduced frequency of dosing.

PEGylation technology has been advantageously applied to therapeutic proteins and oligonucleotides to provide new drugs that have been approved by the U.S. FDA: adensosine deaminase (Pegademenase), asparaginase (Pegaspargase), G-CSF (Pegfilgrastim), interferon-α2a (Peginterferon-α2a), interferon-α2b (Peginterferon-α2b), hGH (Pegvisomant), anti-VEGF aptamer (Pegaptanib), erythropoietin (PEG-EPO), and anti-TNF α Fab' (Certolizumab).

PEGylated therapeutic enzymes presently approved and on the market include depleting enzymes that are used to eliminate certain amino acids from the blood stream to starve growing tumor cells. Examples include PEG-asparaginase, PEG-methioninase, and PEG-arginine deiminase. For these enzymes, their relatively small amino acid substrates are able to diffuse through the PEG layer, enter the active site of the enzyme, and are effectively disposed of as designed. However, biomolecules requiring polymeric protection and that act on larger substrates have not been able to be developed because of the required level of PEGylation to retain the enzyme in the body, which renders the active site inaccessible.

PEGylation and PEGylated biomolecules are not without their drawbacks. Due to its strong attraction to water, PEG is known to take on a hydrodynamic diameter significantly greater than would be predicted by their molecular weight. This ballooning effect can be attributed to the reduction in the ability of the body to recognize the biomolecule and results in a decrease in the biomolecule's activity.

A murine A7 monoclonal antibody PEGylated with ten (10) 5 kDa PEG has an activity that is 10% that of the unmodified antibody. Similarly, an interferon-α2a PEGylated with a single 40 kDa PEG has an activity that is 7% that of the unmodified protein. Clearly, modification or hindrance of a biomolecule's active site resulting from PEGylated is a serious problem to be avoided in the development of a biopharmaceutical product.

Despite the advancement in biopharmaceutical drug development provided by PEGylation, a need exists to further advance biopharmaceutical drug development, to overcome the drawbacks associated with PEGylated drugs, and to provide improved reagent and biopharmaceutical products. The present invention seeks to fulfill this need and provides further related advantages,

SUMMARY OF THE INVENTION

The invention provides polymer biomolecule conjugates, reagents and methods for making the conjugates, and methods for using conjugates.

In one aspect, the invention provides a zwitterionic polymer bioconjugate comprising one or more zwitterionic polymers covalently coupled to a biomolecule.

In one embodiment, the zwitterionic polymer comprises a plurality of repeating units, each repeating unit having the formula:

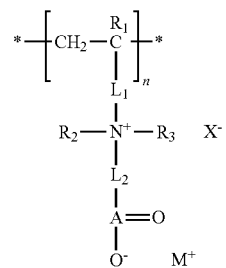

wherein

R₁ is selected from the group consisting of hydrogen, fluorine, trifluoromethyl, C1-C6 alkyl, and C6-C12 aryl groups;

R₂ and R₃ are independently selected from the group consisting of alkyl and aryl, or taken together with the nitrogen to which they are attached form a cationic center;

$L_1$ is a linker that covalently couples the cationic center [N⁺(R₂)(R₃)] to the polymer backbone [—(CH₂—CR₁)$_n$—];

$L_2$ is a linker that covalently couples the anionic center [A(=O)O⁻] to the cationic center;

A is C, SO, SO₂, or PO;

M⁺ is a counterion associated with the (A=O)O⁻ anionic center;

X⁻ is a counter ion associated with the cationic center; and n is an integer from 1 to about 10,000.

In another aspect, the invention provides a mixed charge copolymer bioconjugate comprises one or more mixed charge polymers covalently coupled to a biomolecule.

In one embodiment, the mixed charge copolymer comprises a plurality of repeating units, each repeating unit having the formula:

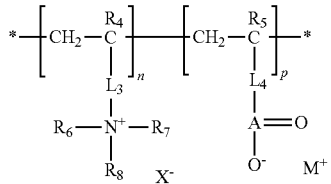

wherein

R₄ and R₅ are independently selected from hydrogen, fluorine, trifluoromethyl, C1-C6 alkyl, and C6-C12 aryl groups;

R₆, R₇, and R₈ are independently selected from alkyl and aryl, or taken together with the nitrogen to which they are attached form a cationic center;

A(=O)—OM) is an anionic center, wherein A is C, SO, SO₂, or PO, and M is a metal or organic counterion;

$L_3$ is a linker that covalently couples the cationic center [N⁺(R₆)(R₇)(R₈)] to the polymer backbone;

$L_4$ is a linker that covalently couples the anionic center [A(=O)—OM] to the polymer backbone;

X⁻ is the counter ion associated with the cationic center;

n is an integer from 1 to about 10,000; and p is an integer from 1 to about 10,000.

For the above conjugates, representative biomolecules include proteins, nucleic acids, carbohydrates, lipids, and small molecules. In certain embodiments, the biomolecule has increased thermal stability relative to its unconjugated form. In certain embodiments, the conjugate resists denaturation by chaotropes and is suitable for protein loading with anionic radiotherapeutics (e.g., $I_{125}^-$ and $I_{135}^-$).

In another aspect, the invention provides compositions that include one or more of the conjugates of the invention and a pharmaceutically accepted carrier or diluent.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

(FIG. 3A) and pCB $R_h$ Eq. (FIG. 3B). Unconjugated CT is included for comparison.

DETAILED DESCRIPTION OF THE INVENTION

Figure 1:
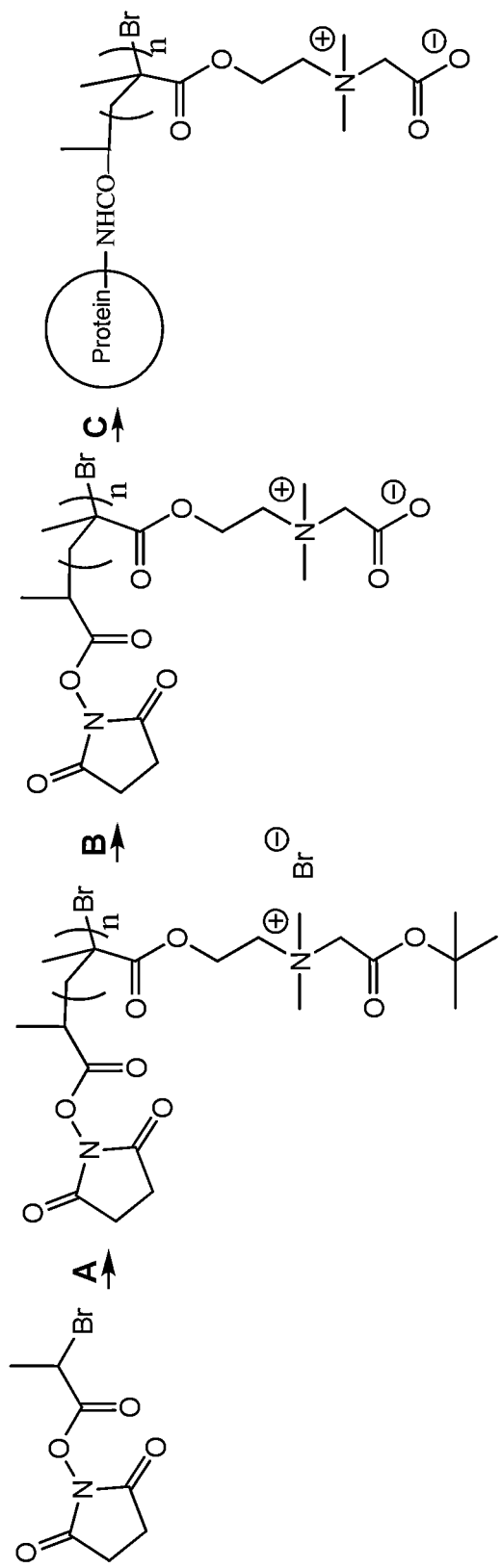
FIG. 1 is a schematic illustration of the preparation of a representative zwitterionic polymer-protein conjugate of the invention. A representative NHS-ester terminated zwitterionic polymer is synthesized by atom transfer radical polymerization using a representative zwitterionic monomer (CBMA) and an NHS-ester initiator. The NHS-ester terminated zwitterionic polymer is conjugated to the protein by reacting the NHS-ester with available amino groups (e.g., -amino groups of lysine residues).

The invention provides polymer biomolecule conjugates, reagents and methods for making the conjugates, and methods for using conjugates.

In one aspect, the invention provides a zwitterionic polymer biomolecule conjugate. As used herein, the term "zwitterionic polymer biomolecule conjugate" or "zwitterionic polymer bioconjugate" refers to a biomolecule that has been modified by conjugation to a zwitterionic polymer.

In another aspect, the invention provides a mixed charge copolymer biomolecule conjugate. As used herein, the term "mixed charge copolymer biomolecule conjugate" or "mixed charge copolymer bioconjugate" refers to a biomolecule that has been modified by conjugation to a mixed charge copolymer.

The biomolecule can be modified to include one or more zwitterionic polymers, or one or more mixed charge polymers, which are covalently coupled to the biomolecule.

Zwitterionic Polymer

The zwitterionic polymer bioconjugate comprises one or more zwitterionic polymers covalently coupled to a biomolecule.

In one embodiment, the zwitterionic polymer comprises a plurality of repeating units, each repeating unit having the formula (I):

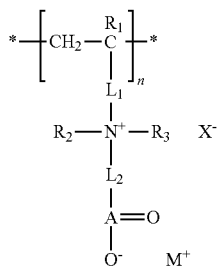

(I)

wherein $R_1$ is selected from the group consisting of hydrogen, fluorine, trifluoromethyl, C1-C6 alkyl, and C6-C12 aryl groups;

$R_2$ and $R_3$ are independently selected from the group consisting of alkyl and aryl, or taken together with the nitrogen to which they are attached form a cationic center;

$L_1$ is a linker that covalently couples the cationic center $[N^{30}\ (R_2)(R_3)]$ to the polymer backbone $[-(CH_2-CR_1)_n-]$;

$L_2$ is a linker that covalently couples the anionic center $[A(=O)O-^-]$ to the cationic center;

A is C, SO, $SO_2$, or PO;

$M^+$ is a counterion associated with the $(A=O)O^-$ anionic center;

$X^-$ is a counter ion associated with the cationic center;

n is an integer from 1 to about 10,000; and

* represents the point at which the repeating unit is covalently linked to the next.

Mixed Charge Copolymer

The mixed charge copolymer bioconjugate comprising one or more mixed charge copolymers covalently coupled to a biomolecule.

As used herein, the term "mixed charge copolymer" refers to a copolymer having a polymer backbone, a plurality of positively charged repeating units, and a plurality of negatively charged repeating units. In the practice of the invention, these copolymers may be prepared by polymerization of an ion-pair comonomer.

The mixed charge copolymer includes a plurality of positively charged repeating units, and a plurality of negatively charged repeating units. In one embodiment, the mixed charge copolymer is substantially electronically neutral. As used herein, the term "substantially electronically neutral" refers to a copolymer that imparts advantageous nonfouling properties to the copolymer. In one embodiment, a substantially electronically neutral copolymer is a copolymer having a net charge of substantially zero (i.e., a copolymer about the same number of positively charged repeating units and negatively charged repeating units). In one embodiment, the ratio of the number of positively charged repeating units to the number of the negatively charged repeating units is from about 1:1.1 to about 1:0.5. In one embodiment, the ratio of the number of positively charged repeating units to the number of the negatively charged repeating units is from about 1:1.1 to about 1:0.7. In one embodiment, the ratio of the number of positively charged repeating units to the number of the negatively charged repeating units is from about 1:1.1 to about 1:0.9.

Ion Pair Comonomers

In one embodiment, the copolymers are prepared by copolymerization of suitable polymerizable ion pair comonomers.

Representative ion-pair comonomers useful in the invention have formulas (II) and (III):

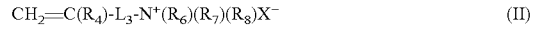

In this embodiment, the crosslinked polymer (e.g., hydrogel) has repeating units having formula (IV):

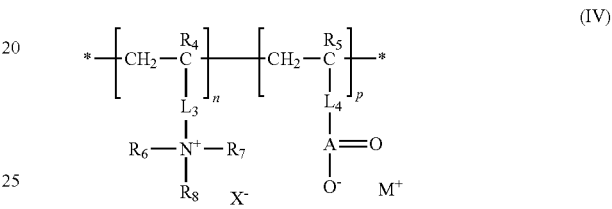

wherein $R_4$ and $R_5$ are independently selected from hydrogen, fluorine, trifluoromethyl, C1-C6 alkyl, and C6-C12 aryl groups;

$R_6$, $R_7$, and $R_8$ are independently selected from alkyl and aryl, or taken together with the nitrogen to which they are attached form a cationic center;

$A(=O)-OM)$ is an anionic center, wherein A is C, SO, $SO_2$, or PO, and M is a metal or organic counterion;

$L_3$ is a linker that covalently couples the cationic center $[N^+(R_6)(R_7)(R_8)]$ to the polymer backbone;

$L_4$ is a linker that covalently couples the anionic center $[A(=O)-OM]$ to the polymer backbone;

$X^-$ is the counter ion associated with the cationic center;

n is an integer from 1 to about 10,000;

p is an integer from 1 to about 10,000; and

* represents the point at which the repeating units is covalently linked to the next.

In one embodiment, $R_7$ and $R_8$ are C1-C3 alkyl.

$R_6$, $R_7$, and $R_8$ are independently selected from alkyl and aryl, or taken together with the nitrogen to which they are attached form a cationic center. In one embodiment, $R_6$, $R_7$, and $R_8$ are C1-C3 alkyl.

In certain embodiments, $L_3$ is selected from the group consisting of $-C(=O)O-(CH_2)_n-$ and $-C(=O)NH-(CH_2)_n-$, wherein n is an integer from 1 to 20. In certain embodiments, $L_3$ is $-C(=O)O-(CH_2)_n-$, wherein n is 1-6.

In certain embodiments, $L_4$ is a C1-C20 alkylene chain. Representative $L_4$ groups include $-(CH_2)_n-$, where n is 1-20 (e.g., 1, 3, or 5)

In certain embodiments, A is C or SO.

In certain embodiments, n is an integer from 5 to about 5,000.

In one embodiment, $R_4$, $R_5$, $R_6$, $R_7$, and $R_8$ are methyl, $L_3$ is $-C(=O)O-(CH_2)_2-$, and $L_4$ is $-CH_2-$, $A_1$ is C or SO, and n is an integer from 5 to about 5,000.

In the above formulas, the polymer backbones include vinyl backbones (i.e., $-C(R')(R'')-C(R''')(R'''')-$, where R', R'', R''', and R'''' are independently selected from hydrogen, alkyl, and aryl) derived from vinyl monomers (e.g., acrylate, methacrylate, acrylamide, methacrylamide, styrene).

In the above formulas, $N^+$ is the cationic center. In certain embodiments, the cationic center is a quaternary ammonium (e.g., N bonded to $L_1$, $R_2$, $R_3$, and $L_2$). In addition to ammonium, other useful cationic centers (e.g., $R_2$ and $R_3$ taken together with N) include imidazolium, triazaolium, pyridinium, morpholinium, oxazolidinium, pyrazinium, pyridazinium, pyrimidinium, piperazinium, and pyrrolidinium.

$R_1$-$R_8$ are independently selected from hydrogen, alkyl, and aryl groups. Representative alkyl groups include C1-C10 straight chain and branched alkyl groups. In certain embodiments, the alkyl group is further substituted with one of more substituents including, for example, an aryl group (e.g., —$CH_2C_6H_5$, benzyl). In one embodiment, $R_2$ and $R_3$, and $R_6$, $R_7$, and $R_8$, are methyl. In one embodiment, $R_1$-$R_8$ are methyl. Representative aryl groups include C6-C12 aryl groups including, for example, phenyl. For certain embodiments of the above formulas, $R_2$ and $R_3$, and/or $R_6$, $R_7$, and $R_8$ are taken together with $N^+$ form the cationic center.

$L_1$ is a linker that covalently couples the cationic center to the polymer backbone. In certain embodiments, $L_1$ includes a functional group (e.g., ester or amide) that couples the remainder of $L_1$ to the polymer backbone (or polymerizable moiety for the monomers). In addition to the functional group, $L_1$ can include an C1-C20 alkylene chain. Representative $L_1$ groups include —C(=O)O—$(CH_2)_n$— and —C(=O)NH—$(CH_2)_n$—, where n is 1-20 (e.g., n=2).

$L_2$ is a linker that covalently couples the cationic center to the anionic group. $L_2$ can be a C1-C20 alkylene chain. Representative $L_2$ groups include —$(CH_2)_n$—, where n is 1-20 (e.g., 1, 3, or 5).

$L_3$ is a linker that covalently couples the cationic center to the polymer backbone. In certain embodiments, $L_3$ includes a functional group (e.g., ester or amide) that couples the remainder of $L_3$ to the polymer backbone (or polymerizable moiety for the monomers). In addition to the functional group, $L_3$ can include an C1-C20 alkylene chain. Representative $L_3$ groups include —C(=O)O—$(CH_2)_n$— and —C(=O)NH—$(CH_2)_n$—, where n is 1-20 (e.g., n=2).

$L_4$ is a linker that covalently couples the anionic group to the polymer backbone. $L_4$ can be a C1-C20 alkylene chain. Representative $L_4$ groups include —$(CH_2)_n$—, where n is 1-20 (e.g., 1, 3, or 5).

Representative alkyl groups include C1-C30 straight chain and branched alkyl groups. In certain embodiments, the alkyl group is further substituted with one of more substituents including, for example, an aryl group (e.g., —$CH_2C_6H_5$, benzyl).

Representative aryl groups include C6-C12 aryl groups including, for example, phenyl including substituted phenyl groups (e.g., benzoic acid).

$X^-$ is the counter ion associated with the cationic center. The counter ion can be the counter ion that results from the synthesis of the cationic polymers or the monomers (e.g., $Cl^-$, $Br^-$, $I^-$). The counter ion that is initially produced from the synthesis of the cationic center can also be exchanged with other suitable counter ions. Representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions also can be chosen from chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof. Other suitable counter ions include salicylic acid (2-hydroxybenzoic acid), benzoate, and lactate.

The size (e.g., n or $M_n$) of the zwitterionic polymer conjugated to the biomolecule can be varied and depends on the nature of the biomolecule.

For the polymers useful in the invention, the degree of polymerization (DP or n), number average molecular weight ($M_n$), and the ratio of weight average and number average molecular weights ($M_w/M_n$.), also known as polydispersity index, can vary. In one embodiment, the polymers have a degree of polymerization (n) from 1 to about 10,000. In one embodiment, n is from about 10 to about 5,000. In another embodiment, n is from about 100 to about 3,500. In one embodiment, the polymers have a number average molecular weight ($M_n$) of from about 200 to about 2,000,000 Da. In one embodiment, $M_n$ is from about 2,000 to about 100,000 Da. In another embodiment, $M_n$ is from about 20,000 to about 80,000 Da. In one embodiment, the polymers have a ratio of weight average and number average molecular weight ($M_w/M_n$.) of from about 1.0 to about 2.0. In one embodiment, $M_w/M_n$. is from about 1.1 to about 1.5. In another embodiment, $M_w/M_n$. is from about 1.2 to about 2.0.

Biomolecules

As noted above, the zwitterionic polymer bioconjugate comprises one or more zwitterionic polymers covalently coupled to a biomolecule. Suitable biomolecules include biopolymers (e.g., proteins, peptides, oligonucleotides, polysaccharides), lipids, and small molecules.

Exemplary biomolecules that may be used in accordance with the present invention include proteins (including multimeric proteins, protein complexes, peptides), nucleic acids, lipids, carbohydrates, and small molecules.

Protein Agents.

In some embodiments, the biomolecule is a protein or peptide. The terms "protein," "polypeptide," and "peptide" can be used interchangeably. In certain embodiments, peptides range from about 5 to about 5000, 5 to about 1000, about 5 to about 750, about 5 to about 500, about 5 to about 250, about 5 to about 100, about 5 to about 75, about 5 to about 50, about 5 to about 40, about 5 to about 30, about 5 to about 25, about 5 to about 20, about 5 to about 15, or about 5 to about 10 amino acids in size.

Polypeptides may contain L-amino acids, D-amino acids, or both and may contain any of a variety of amino acid modifications or analogs known in the art. Useful modifications include, e.g., terminal acetylation, amidation. In some embodiments, polypeptides may comprise natural amino acids, unnatural amino acids, synthetic amino acids, and combinations thereof, as described herein.

In some embodiments, the therapeutic agent may be a hormone, erythropoietin, insulin, cytokine, antigen for vaccination, growth factor. In some embodiments, the therapeutic agent may be an antibody and/or characteristic portion thereof. In some embodiments, antibodies may include, but are not limited to, polyclonal, monoclonal, chimeric (i.e., "humanized"), or single chain (recombinant) antibodies. In some embodiments, antibodies may have reduced effector functions and/or bispecific molecules. In some embodiments, antibodies may include Fab fragments and/or fragments produced by a Fab expression library (e.g. Fab, Fab', F(ab')2, scFv, Fv, dsFv diabody, and Fd fragments).

Nucleic Acid Agents.

In certain embodiments of the invention, the biomolecule is a nucleic acid (e.g., DNA, RNA, derivatives thereof). In some embodiments, the nucleic acid agent is a functional RNA. In general, a "functional RNA" is an RNA that does not code for a protein but instead belongs to a class of RNA molecules whose members characteristically possess one or more different functions or activities within a cell. It will be appreciated that the relative activities of functional RNA molecules having different sequences may differ and may depend at least in part on the particular cell type in which the RNA is present. Thus the term "functional RNA" is used herein to refer to a class of RNA molecule and is not intended to imply that all members of the class will in fact display the activity characteristic of that class under any particular set of conditions. In some embodiments, functional RNAs include RNAi-inducing entities (e.g., short interfering RNAs (siRNAs), short hairpin RNAs (shRNAs), and microRNAs), ribozymes, tRNAs, rRNAs, RNAs useful for triple helix formation.

In some embodiments, the nucleic acid agent is a vector. As used herein, the term "vector" refers to a nucleic acid molecule (typically, but not necessarily, a DNA molecule) which can transport another nucleic acid to which it has been linked. A vector can achieve extra-chromosomal replication and/or expression of nucleic acids to which they are linked in a host cell. In some embodiments, a vector can achieve integration into the genome of the host cell.

In some embodiments, vectors are used to direct protein and/or RNA expression. In some embodiments, the protein and/or RNA to be expressed is not normally expressed by the cell. In some embodiments, the protein and/or RNA to be expressed is normally expressed by the cell, but at lower levels than it is expressed when the vector has not been delivered to the cell. In some embodiments, a vector directs expression of any of the functional RNAs described herein, such as RNAi-inducing entities, ribozymes.

Carbohydrate Agents.

In some embodiments, the biomolecule is a carbohydrate. In certain embodiments, the carbohydrate is a carbohydrate that is associated with a protein (e.g. glycoprotein, proteogycan). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

Lipid Agents.

In some embodiments, the biomolecule is a lipid. In certain embodiments, the lipid is a lipid that is associated with a protein (e.g., lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g., vitamin E), phospholipids, sphingolipids, and lipoproteins.

In some embodiments, the lipid may comprise one or more fatty acid groups or salts thereof. In some embodiments, the fatty acid group may comprise digestible, long chain (e.g., C8-C50), substituted or unsubstituted hydrocarbons. In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

Small Molecule Agents.

In some embodiments, the therapeutic agent is a small molecule and/or organic compound with pharmaceutical activity. In some embodiments, the therapeutic agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g., cell growth inhibitors and anti-adhesion molecules), inhibitor of DNA, RNA, or protein synthesis.

In certain embodiments, a small molecule agent can be any drug. In some embodiments, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

A more complete listing of classes and specific drugs suitable for use in the present invention may be found in "Pharmaceutical Drugs: Syntheses, Patents, Applications" by Axel Kleemann and Jurgen Engel, Thieme Medical Publishing, 1999, and "The Merck Index: An Encyclopedia of Chemicals, Drugs, and Biologicals, Budavari et al. (eds.), CRC Press, 1996, both of which are incorporated herein by reference.

Biomolecules that can be advantageously conjugated with one or more zwitterionic polymer include biopharmaceuticals that have been approved for use. Biomolecules and biopharmaceuticals that have been PEGylated exemplify a class of biopharmaceuticals suitable for conjugation with one or more zwitterionic polymers to provide a zwitterionic polymer bioconjugate of the invention.

Conjugation Methods

The zwitterionic polymer can be conjugated to the biomolecule by covalent coupling of a suitably reactive polymer (e.g., active ester) with a native biomolecule or biomolecule modified to include a suitably reactive group (e.g., amino group of a native lysine residue for a protein or an amino group that has been incorporated into a protein or oligonucleotide). The preparation of a representative zwitterionic protein conjugate by conjugating a reactive ester (NHS) of a zwitterionic polymer to a generic protein (e.g., through available lysine groups) is illustrated schematically in FIG. 1. The coupling of a representative zwitterionic polymer (end terminal NHS ester of a polycarboxybetaine) to a representative biomolecule (enzyme CT) is described in Example 1.

Alternatively, the zwitterionic polymer bioconjugate can be prepared by covalently coupling one or more polymerization initiators to the biomolecule followed by polymerization using a suitable zwitterionic monomer to graft the polymer from the biomolecule (i.e., in situ polymerization). In this method, the one or more polymerization initiators are coupled to the biomolecule in the same way as described above for the direct conjugation of the polymer to the biomolecule. The in situ polymerization method may only be used for biomolecules that are stable to the reaction conditions required for polymerization.

Pharmaceutical Compositions

In another aspect, the invention provides a composition that includes the zwitterionic polymer bioconjugate of the invention and a pharmaceutically acceptable carrier or diluent. Suitable carriers and diluents include those known in the art, such as saline and dextrose.

Methods for Administration/Treatment

In another aspect of the invention, methods for administration and treatment are provided.

In one embodiment, the invention provides a method for administration a zwitterionic polymer bioconjugate comprising administering a zwitterionic polymer bioconjugate of the invention to a subject in need thereof.

In one embodiment, the invention provides a method for treating a disease or condition treatable by administration of a biomolecule. In the method, a zwitterionic polymer conjugate of the biomolecule is administered to a subject in need thereof.

The following is a description of the preparation and properties of a representative zwitterionic polymer bioconjugate of the invention. In the following description, the biomolecule is exemplified by an enzyme, alpha-chymotrypsin (CT). Certain properties of the bioconjugate are compared to a corresponding PEGylated conjugate.

Stability.

Figure 3A:
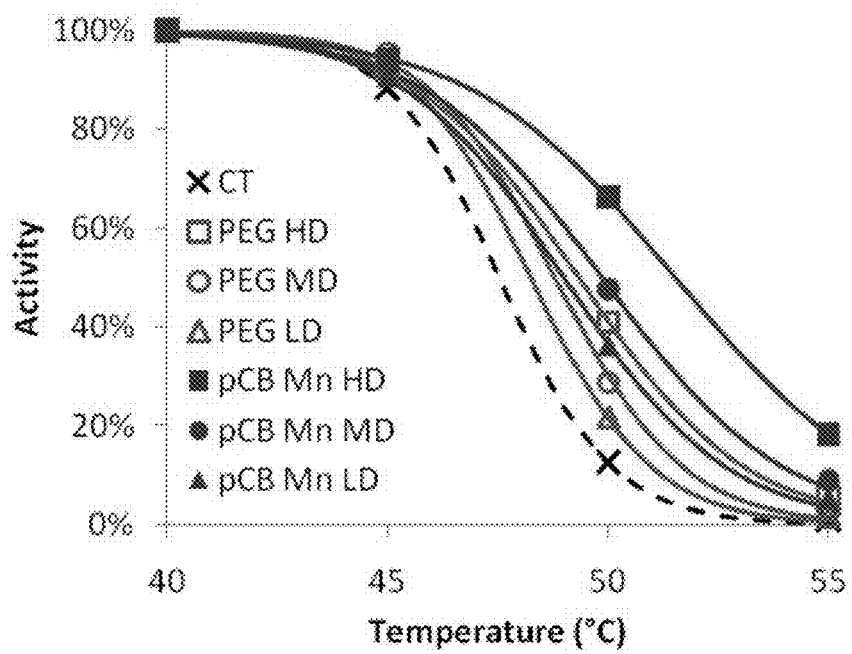
FIGS. 3A and 3B compare thermal stability for CT-PEG (LD, MD, and HD) and representative zwitterionic polymer-protein conjugates of the invention, CT-pCB (LD, MD, and HD). CT-pCB conjugates are pCB $M_n$ Eq.
Figure 3B:
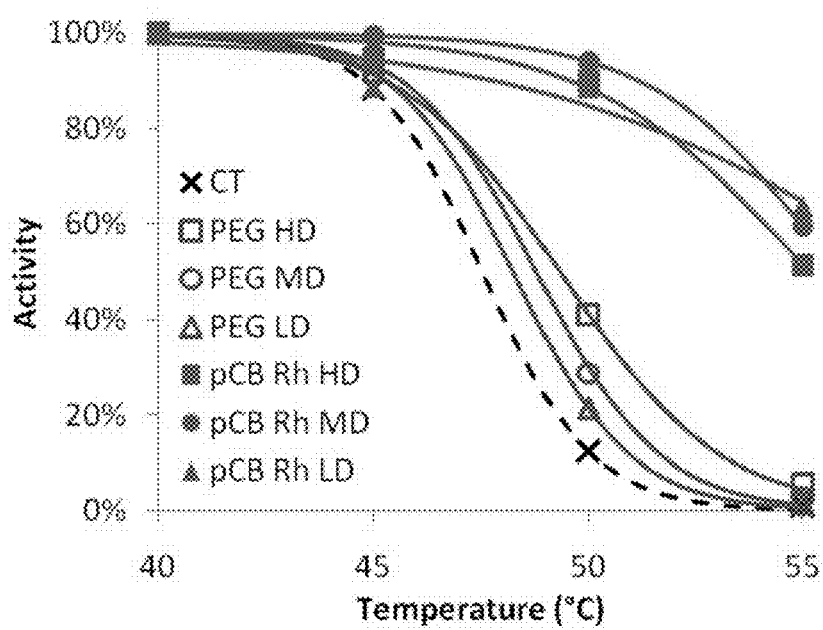

A thermal stability test was performed, measuring the effect of temperature on enzyme activity. N-Succinyl-Ala-Ala-Pro-Phe p-nitroanilide (SEQ ID NO:1), a 625 Da peptide-based substrate was used to measure activity. From the data in FIG. 3A, it is seen that both pCB and PEG have stabilizing effects at elevated temperatures. Although PEG is a known stabilizing agent, pCB $M_n$Eq. conjugates were seen to provide even further improvement. In FIG. 3B it can be seen with pCB $R_h$ Eq significant thermal stability is measured when compared to the previous two conjugates.

Figure 4:
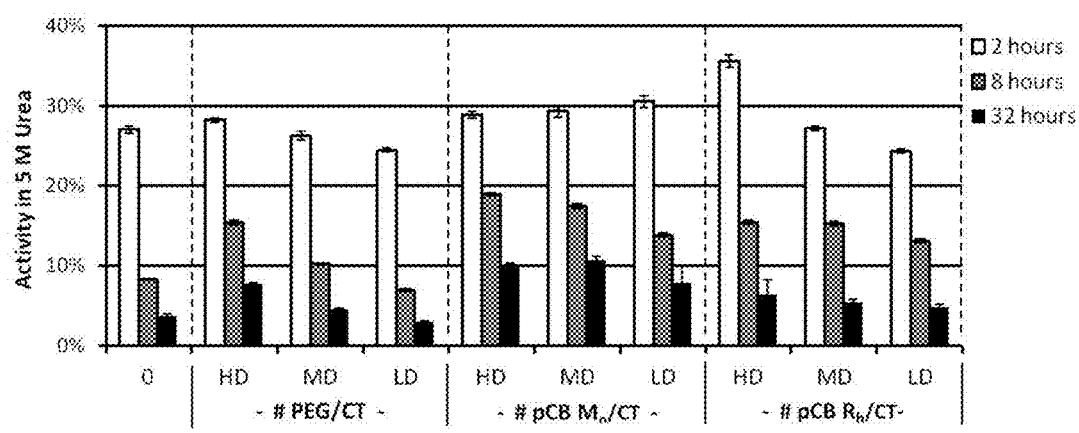
FIG. 4 compares chemical stability threw incubation in urea for CT-PEG (LD, MD, and HD) and representative zwitterionic polymer-protein conjugates of the invention, CT-pCB (LD, MD, and HD). CT-pCB conjugates are pCB $M_n$ Eq. and pCB $R_h$ Eq. Unconjugated CT is included for comparison.

Urea, as a denaturant, is theorized to interact with the backbone of proteins and known to cause unfolding and loss of function. To fully stress the stability of the prepared conjugates, a nearly saturated urea solution was used to measure enzyme activity in situ. The results can be seen in FIG. 4. Time points of 2, 8 and 32 hours were chosen. At early time points no significant differences were seen. At 8 and 32 hours, greater instability was seen in the CT control and lower conjugated PEG samples. All pCB conjugates showed increased stability compared to the control even at lower degrees of conjugation. Only the highly conjugated PEG samples (HD) had activity comparable to all the other pCB conjugates. This shows that CT-pCB conjugates have a very unique ability to chemically stabilize proteins even with very little attached polymer.

Figure 5:
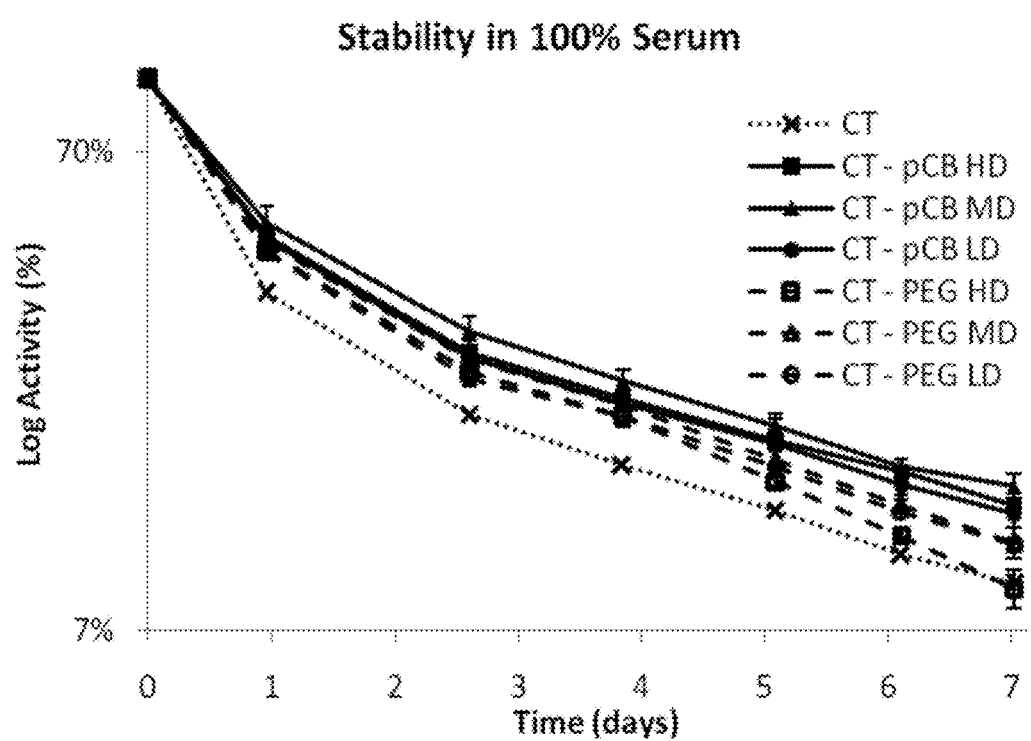
FIG. 5 compares stability of CT-PEG (LD, MD, and HD) and representative zwitterionic polymer-protein conjugates of the invention, CT-pCB (LD, MD, and HD), in 100% serum over seven days. Unconjugated CT is included for comparison.

FIG. 5 shows the serum stability of CT conjugates over a one week period. On day seven it can be seen that all pCB conjugates have a higher retained activity than all the PEG conjugates including the unconjugated control.

Kinetics and Affinity.

For kinetic analysis, CT-PEG conjugates were compared to CT-pCB conjugates of equivalent molecular weight (pCB $M_n$ Eq) and equivalent hydrodynamic size (pCB $R_h$ Eq). Two substrates were used to evaluate the kinetic effects of the polymers: N-Succinyl-Ala-Ala-Pro-Phe p-nitroanilide (SEQ ID NO:1), a 625 Da peptide-based substrate, and resorufin bromoacetate, a smaller (335 Da), non-peptide-based substrate. Resorufin bromoacetate was included as a negative control knowing that small, more hydrophobic substrates are much less inhibited to complex with enzymes by conjugated polymer.

Figure 6A:
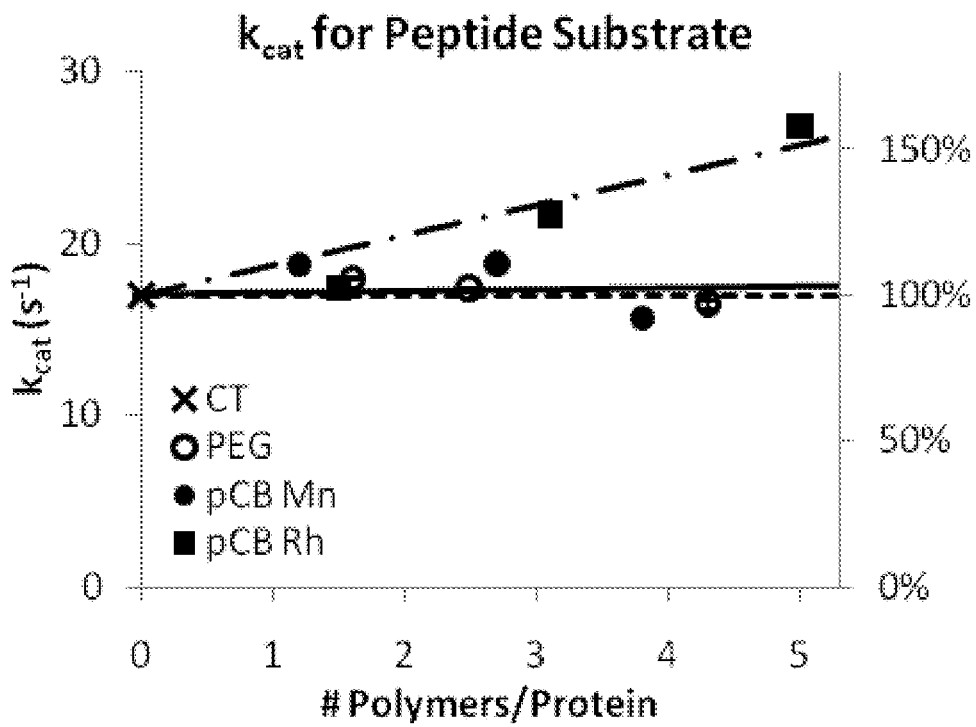
FIGS. 6A and 6B compare the effect of polymer type and degree of conjugation on $k_{cat}$ with a peptide-based substrate (FIG. 6A) and a small molecule substrate (FIG. 6B).
Figure 6B:
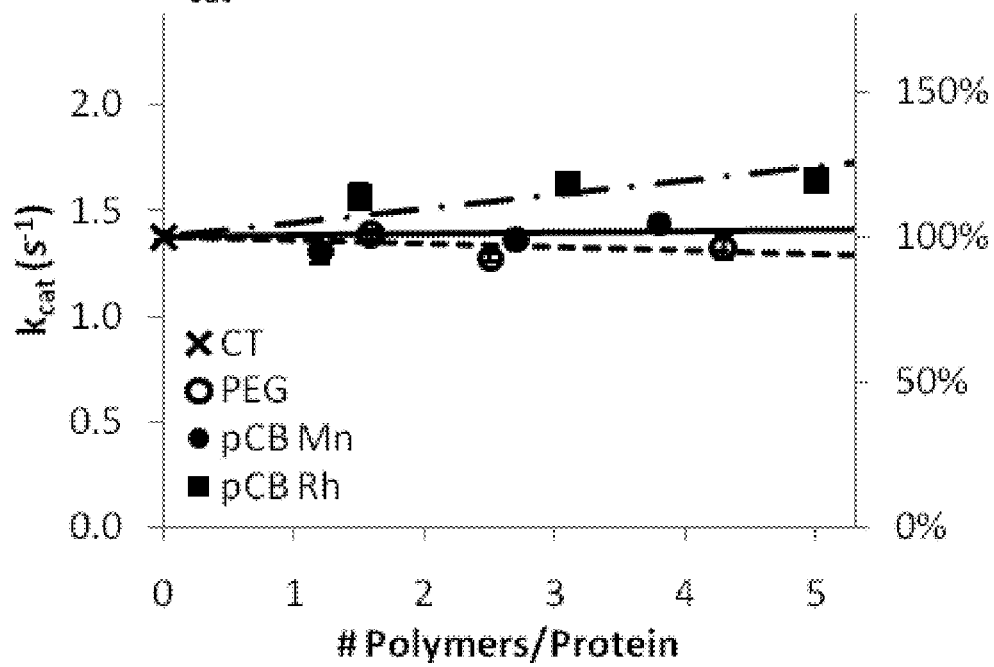

FIG. 6 shows $k_{cat}$ values for all conjugates tested. $k_{cat}$ is the maximum rate of substrate conversion into product. This is independent of the substrate's ability to access the active site, which is represented by $K_m$. $k_{cat}$ occurs post-binding. This can be observed when substrate concentrations are very high. An increase in $k_m$ represents a difference inherent to the enzyme-substrate complex. From FIG. 6 is can be seen that all PEG and pCB $M_n$ Eq conjugates do not show significant change in $k_{cat}$. For these conjugates, the polymers act passively. However, for the pCB $R_h$ Eq samples, there appears to be an increase in $k_{cat}$. This is evidence of the polymer acting directly on the enzyme-substrate complex. For the peptide substrate, the increase in $k_{cat}$ is more apparent and correlates more with the degree of conjugation. This is hypothesized to be due to the substrates amide chemistry, and shows that the polymer's effect on the enzyme and the peptide substrate are additive.

Figure 7A:
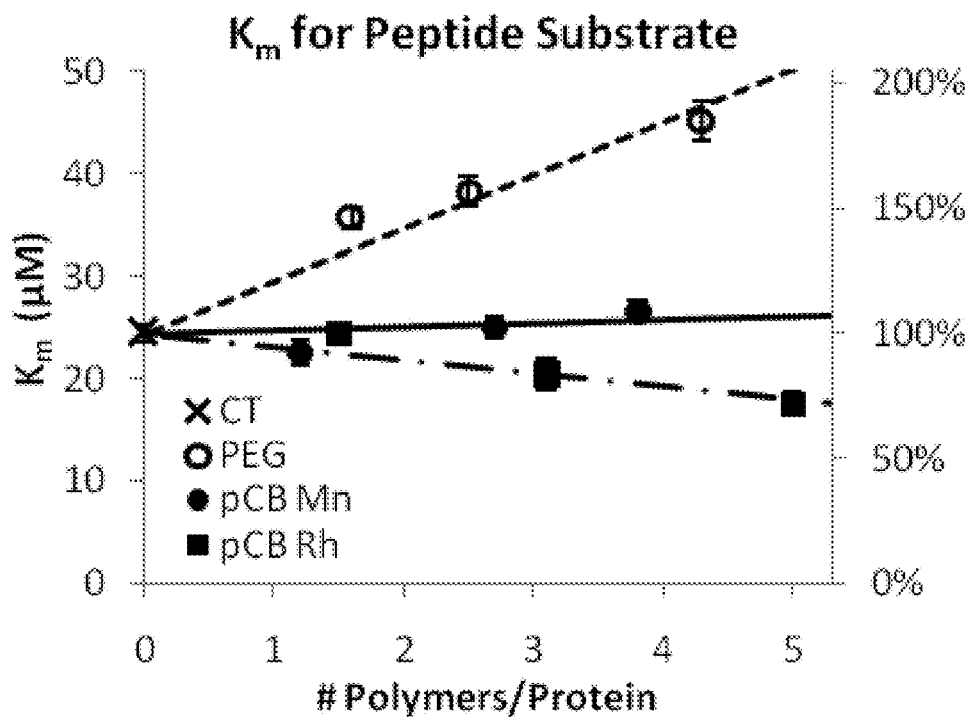
FIGS. 7A and 7B compare the effect of polymer type and degree of conjugation on Michaelis Constant ($k_m$) with a peptide-based substrate (FIG. 7A) and a small molecule substrate (FIG. 7B).
Figure 7B:
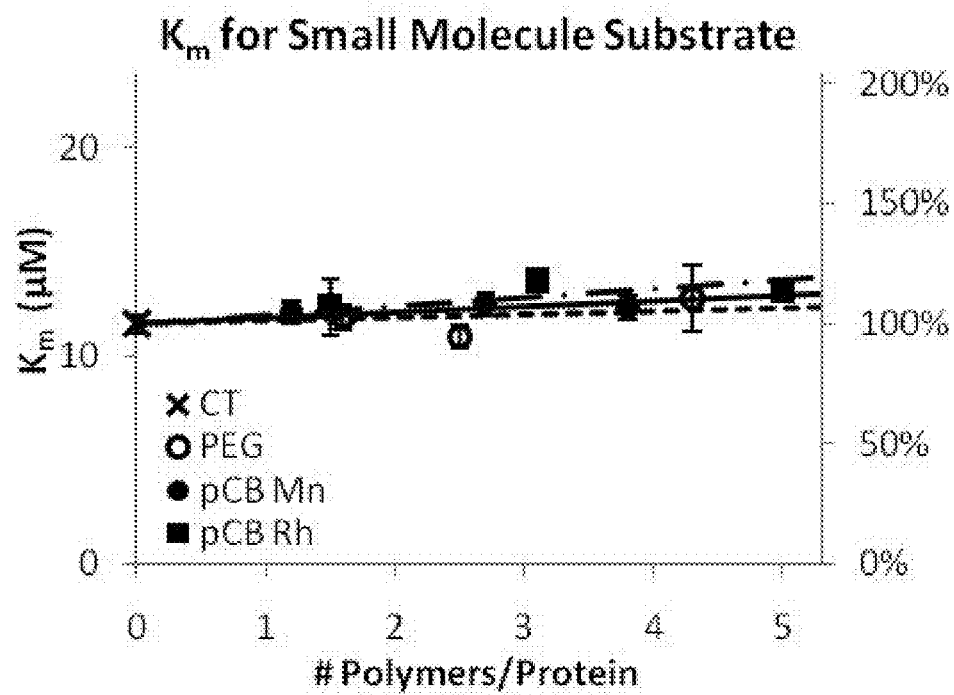

FIG. 7 shows the Michaelis Constant ($K_m$) values for all polymer protein conjugates. $K_m$ is the substrate concentration at which 50% maximal activity ($k_{cat}$) is reached and approximates the affinity of substrate for the enzyme. As expected with the peptide based substrate, PEG has increasingly adverse effects, shown by an increase in $K_m$ with increasing incorporation of polymer. However both CT-pCB conjugates were seen not to have any inhibitory effects. In fact, $K_m$ for the pCB $R_h$ Eq conjugates was seen to decrease as more polymers were incorporated onto the protein. $K_m$ is greatly affected by the size and chemistry of conjugated polymers. As seen in the negative control, there is little trend with the small molecule substrate in comparison. More hydrophobic small molecule substrates are known to diffuse very easily in and out of the polymer shell of enzyme-polymer conjugates.

Figure 8A:
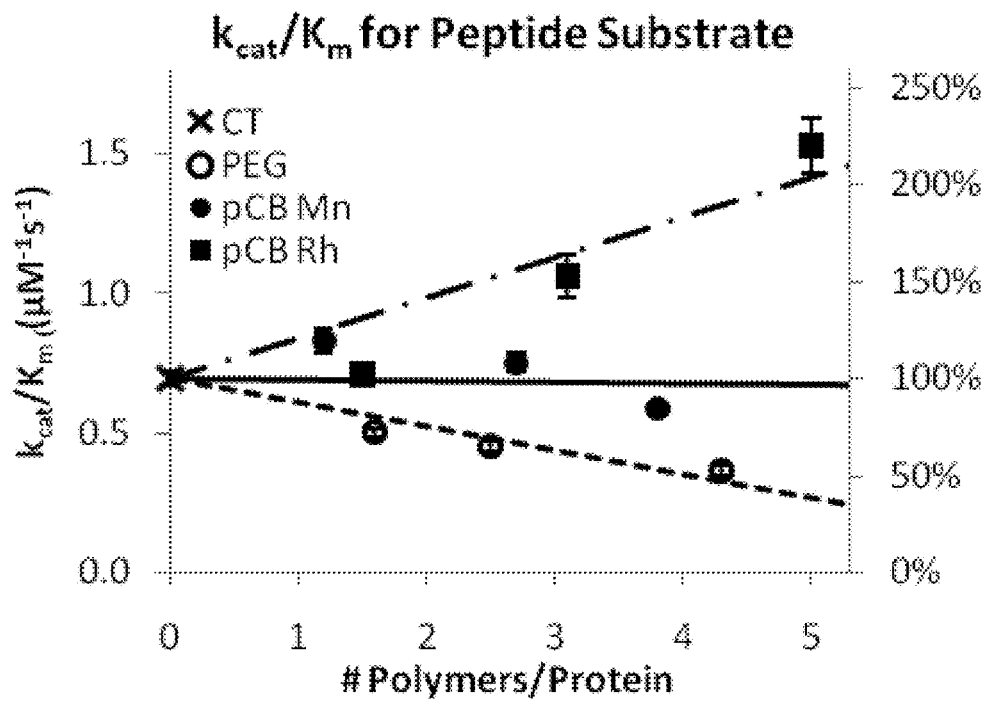
FIGS. 8A and 8B compare the effect of polymer type and degree of conjugation on catalytic efficiency ($k_{cat}/k_m$) with a peptide-based substrate (FIG. 8A) and a small molecule substrate (FIG. 8B).
Figure 8B:
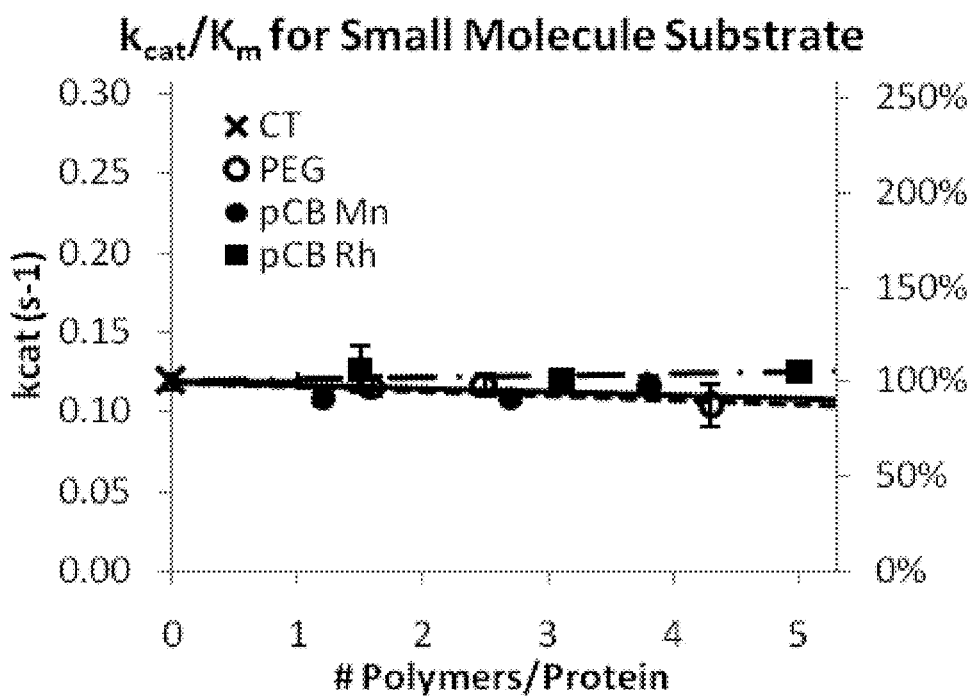

FIG. 8 shows the catalytic efficiency ($k_{cat}/K_m$) for all polymer protein conjugates. This is a universal term to define the total system's efficiency on catalyzing a substrate. These take into account the enzyme's ability to complex with a substrate and effectively convert it into product. Due to the combination of reasons mentioned above, the increase in $K_m$ has resulted in low catalytic efficiencies for PEG conjugates. In contrast, the decrease in $K_m$ and increase in $k_{cat}$ for the pCB $R_h$ Eq has resulted in a large increase in catalytic efficiency. To note, the highly conjugated PEG conjugate is seen to have a 47.6% reduction in catalytic efficiency, while the highly conjugated pCB $R_h$ Eq conjugate is seen to have a 220.4% increase in activity.

The following examples are provided for the purpose of illustrating, not limiting, the invention.

EXAMPLES

Example 1

The Preparation and Characterization of a Representative Zwitterionic Polymer Protein Conjugate

In this example, the preparation and characterization of a representative zwitterionic polymer protein conjugate of the invention, pCB-CT, is described.

Synthesis of NHS Terminated Carboxybetaine Polymers.

N-Hydroxysuccinimide (2.26 g, 19.6 mmol) and 2-bromopropionic acid (1.45 ml, 16.4 mmol) were dissolved, in 500 ml of anhydrous dichloromethane in a round-bottomed flask, with a magnetic stirrer. The flask was cooled to 0° C. and a solution of N,N'-dicyclohexylcarbodiimide (3.35 g, 16.34 mmol) in DCM (25 ml) was added dropwise. After stirring at room temperature overnight the reaction mixture was filtered and the solvent removed under reduced pressure to give a yellow solid. The product was further purified by flash chromatography. Obtained 2.4 g of white solid (9.63 mmol, yield=59%). $^1$H NMR (CDCl$_3$) (ppm): 1.97 (d, 3H, CH(C$\underline{H}_3$)Br), 2.88 (s, 4H), 4.62 (q, 1H, C$\underline{H}$(CH$_3$)Br).

Atom transfer radical polymerization was carried out in anhydrous dimethylformamide (DMF) using a Cu(1)Br/HMTETA catalyst (FIG. 1A). In a typical polymerization, DMF and the liquid HMTETA ligand are separately purged of oxygen by bubbling with nitrogen. 1 g (3.67 mmol) of CBMA-1-tBut monomer and 125 mg (0.5 mmol) of NHS-initiator were added to a Schlenk tube. To a second Schlenk tube was added 71.7 mg (0.5 mmol) of Cu(1)Br. Both tubes were deoxygenated by cycling between nitrogen and vacuum three times. 8 and 2 mL of deoxygenated DMF were added to the monomer/initiator and Cu(1)Br tubes respectively. 136 uL (0.5 mmol) of deoxygenated HMTETA was added to the Cu(1)Br containing solution and was stirred for 30 min under nitrogen protection. The catalyst solution (Cu(1)/HMTETA) was then all added to the monomer/initiator solution to start the reaction. The reaction was run to completion at room temperature with monitoring by NMR. The polymer synthesis is unique because of the use of a protected zwitterionic monomer for controlled polymerization in organic solvent. This is important in treating reactive ester terminated polymers because deactivation of the ester can occur in more aqueous solvents (e.g., water and methanol). Post polymer modification, to remove the protecting monomer group in trifluoroacetic acid (TFA), also does not hydrolyze the active ester. Other zwitterions are unable to remain soluble in organic solvents. This protection method offers a solution to this problem.

After polymerization, the reaction was fully precipitated in ethyl ether. The precipitate was then dried under vacuum and redissolved in minimal DMF (3-5 mL). This solution was vortexed until fully dissolved and precipitated in acetone to remove the soluble catalyst and trace monomer. This was repeated for a total of 3 times to fully remove the catalyst. The remaining ester polymer was dried overnight under vacuum and analyzed by NMR.

To hydrolyze the tert-butyl group, 500 mg NHS-pCBMA-1-tBut was dissolved in 5 mL trifluoroacetic acid (FIG. 1B). This was allowed to sit for 2 hours. The solution was then precipitated in ethyl ether, dried overnight under vacuum and subsequently analyzed by NMR and GPC.

Preparation and Analysis of Carboxybetaine-Protein Conjugates.

For these experiments, a molecular weight of 5 kDa was chosen to be used to compare the effects of PEG and pCB. Due to the different solution conformations between pCB and PEG, the molecular weights determined by GPC vary greatly when compared to the NMR determined molecular weights. PEG is known to take on a much more inflated conformation in solution while pCB is more condensed. This can be seen between the "PEG" and "pCB $M_n$ Eq" GPC molecular weights in Tables 1 and 2. pCB $M_n$ Eq is the molecular weight equivalent to PEG and used in the thermal, urea and serum stability testing. However, pCB conjugates with a larger pCB polymer were also prepared ("pCB $R_h$ Eq") with equivalent size determined by GPC for kinetic analysis. Only the pCB $M_n$ Eq was used the stability studies to prove the smaller of the two prepared pCB polymers still had more advantageous effects when compared to 5 kDa PEG.

TABLE 1

Measured number of polymers conjugated per enzyme by TNBS assay. Additional pCB polymer prepared as a hydrodynamic size equivalent (pCB $R_h$ Eq) to PEG.

| | Polymer number/protein | | |
|---|---|---|---|
| | PEG | pCB $M_n$ Eq | pCB $R_h$ Eq |
| High Density (HD) | 4.3 | 3.8 | 5 |
| Medium Density (MD) | 2.5 | 2.7 | 3.1 |
| Low Density (LD) | 1.6 | 1.2 | 1.5 |

TABLE 2

Molecular weights determined by GPC and NMR (*$M_n$ as received). Additional pCB polymer prepared as a hydrodynamic size equivalent (pCB $R_h$ Eq) to PEG.

| | NMR | GPC | |
|---|---|---|---|
| Polymer | $M_n$ (kDa) | $M_n$ (kDa) | $M_w/M_n$ |
| PEG | 5.0* | 4.9 | 1.01 |
| pCB $M_n$ Eq (PEG molecular weight equiv) | 4.2 | 2.5 | 1.04 |
| pCB $R_h$ Eq (PEG hydrodynamic size equiv) | 12.0 | 6.7 | 1.17 |

Conjugation to surface exposed lysine ε-amino groups of CT with NHS activated pCB and PEG polymers. CT was prepared at 5 mg/mL in 200 mM HEPES buffer at pH 8.0 (FIG. 1C). Dry polymer was added directly to the enzyme solution. The feed ratios of polymer to protein were adjusted to control the degree of conjugation (number of polymers/CT protein). The reaction solution was stirred for 2 h on ice and then placed in the refrigerator overnight. Conjugates were purified from unreacted polymer by several buffer exchanges with phosphate buffered saline, pH 7.4, using ultrafiltration (30,000 Da MWCO). Glycerol was added at 40% after final filtration and stored at −20° C. The degree of modification (number of polymers/CT protein) was determined by a TNBS assay. The numbers of polymers per protein are set forth in Table 1. Conjugation was also confirmed in the GPC chromatograms (FIG. 2).

Figure 2A:
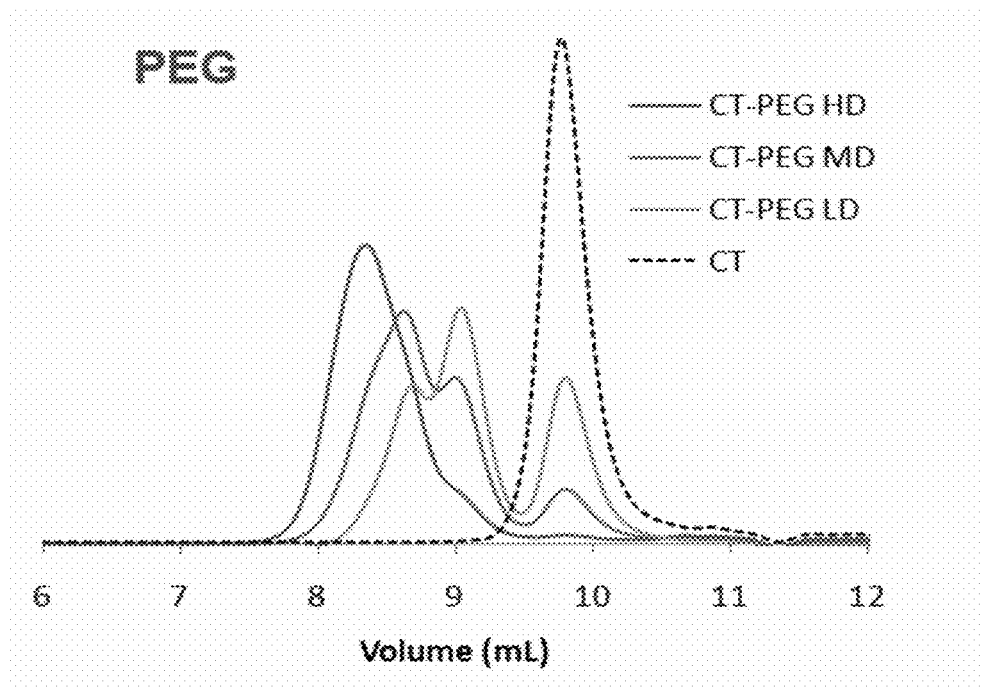
FIGS. 2A and 2B compare gel permeation chromatographs for CT-PEG (LD, MD, and HD) (FIG. 2A) and representative zwitterionic polymer-protein conjugates of the invention, CT-pCB (LD, MD, and HD) (FIG. 2B). CT-pCB conjugates are pCB are $M_n$ Eq. Unconjugated CT is included for comparison.
Figure 2B:
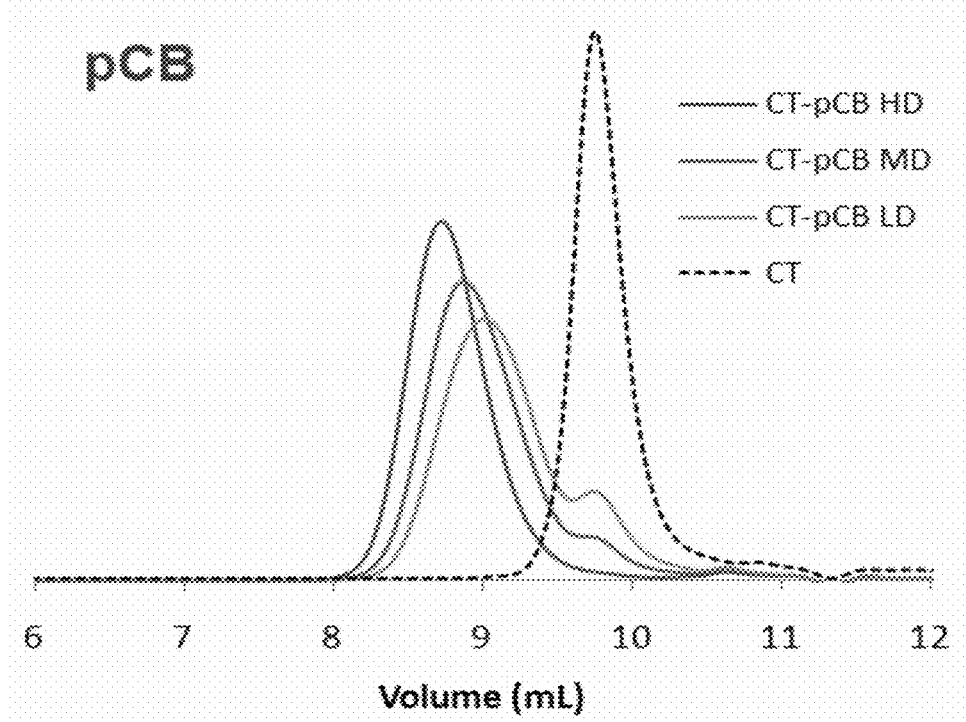

Examples for PEG and pCB $M_n$ Eq. conjugates can be seen in FIG. 2.

Although membrane purification for this system was used, other methods were also addressed. Typical methods for protein purification include tag affinity, ion exchange and size exclusion chromatography. Presenting a unique challenge was ion exchange of the pCb conjugates. Due to the polymer's ionic nature, resolution between conjugates and non-conjugates was very poor. PEG is an uncharged polymer and was shown to have very high resolution. Protein tagging was not appropriate for the model system being used and therefore not tested. Size exclusion for both pCB and Peg conjugates worked well and should be used for all pCB purification needs.

A unique method for purification that is selective ammonium sulfate protein precipitation. Due to the unique kosmotropic characteristics of the pCB polymer, separation by ammonium sulfate protein precipitation works well for this system. PEG is proposed to have the opposite effect and not precipitate as easily by this technique and require other purification methods.

While illustrative embodiments have been illustrated and described, it will be appreciated that various changes can be made therein without departing from the spirit and scope of the invention.

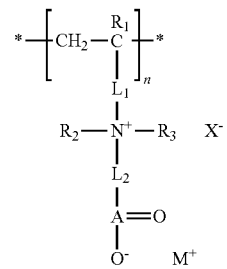

wherein

R$_1$ is selected from the group consisting of hydrogen, fluorine, trifluoromethyl, C1-C6 alkyl, and C6-C12 aryl groups;

R$_2$ and R$_3$ are independently selected from the group consisting of hydrogen, alkyl, and aryl, and taken together with the nitrogen to which they are attached form a cationic center;

L$_1$ is a linker that covalently couples the cationic center [N$^+$(R$_2$)(R$_3$)] to the polymer backbone [—(CH$_2$—CR$_1$)$_n$—];

L$_2$ is a linker that covalently couples the anionic center [A(=O)O$^-$] to the cationic center;

A is C;

M$^+$ is a counterion associated with the (A=O)O$^-$ anionic center;

X$^-$ is a counterion associated with the cationic center; and n is an integer from 1 to about 10,000.

---

---

The embodiments of the invention in which an exclusive property or privilege is claimed are defined as follows:

1. A zwitterionic polymer bioconjugate comprising one or more zwitterionic polymers covalently coupled to a biomolecule, wherein at least one of the zwitterionic polymers is a carboxybetaine, and wherein the biomolecule is an enzyme, a hormone, a cytokine, or a growth factor.

2. The bioconjugate of claim 1, wherein the zwitterionic polymer comprises a plurality of repeating units, each repeating unit having the formula:

3. The bioconjugate of claim 2, wherein R$_1$, R$_2$, and R$_3$ are independently selected from the group consisting of C1-C3 alkyl.

4. The bioconjugate of claim 2, wherein L$_1$ is selected from the group consisting of —C(=O)O—(CH$_2$)$_{n'}$— and —C(=O)NH—(CH$_2$)$_{n'}$—, wherein n' is an integer from 1 to 20.

5. The bioconjugate of claim 2, wherein L$_2$ is —(CH$_2$)$_{n''}$—, where n" is an integer from 1 to 20.

6. A composition, comprising the bioconjugate of claim 1 and a pharmaceutically accepted carrier or diluent.

7. The bioconjugate of claim 1, wherein the bioconjugate of the biomolecule has increased thermal stability relative to unconjugated form of the biomolecule.

* * * * *